(12) United States Patent
Durley et al.

(10) Patent No.: US 6,756,406 B2
(45) Date of Patent: Jun. 29, 2004

(54) 2-AMINO-2-ALKYL-4 HEXENOIC AND HEXYNOIC ACID DERIVATIVES USEFUL AS NITRIC OXIDE SYNTHASE INHIBITORS

(75) Inventors: Richard C. Durley, Chesterfield, MO (US); James Sikorski, Atlanta, GA (US); Donald W. Hansen, Jr., Skokie, IL (US); Michelle A. Promo, Chesterfield, MO (US); Ronald Keith Webber, St. Charles, MO (US); Barnett S. Pitzele, Skokie, IL (US); Alok K. Awasthi, Skokie, IL (US); Alan Moorman, Weldon Springs, MO (US)

(73) Assignee: Pharmacia Corporation, St. Louis, MO (US)

(*) Notice: Subject to any disclaimer, the term of this patent is extended or adjusted under 35 U.S.C. 154(b) by 0 days.

(21) Appl. No.: 09/952,906

(22) Filed: Sep. 15, 2001

(65) Prior Publication Data

US 2002/0128510 A1 Sep. 12, 2002

Related U.S. Application Data

(60) Provisional application No. 60/232,680, filed on Sep. 15, 2000.

(51) Int. Cl.[7] ................ C07D 271/06; C07D 209/48; C07C 251/00; C07C 229/00; A61K 31/195
(52) U.S. Cl. .............. 514/564; 548/131; 548/473; 548/479; 562/560; 562/561; 562/564
(58) Field of Search ............... 518/131, 473, 518/479; 562/560, 561, 564; 514/564

(56) References Cited

U.S. PATENT DOCUMENTS

| | | | |
|---|---|---|---|
| 5,132,453 A | 7/1992 | Griffith | 562/560 |
| 5,863,931 A * | 1/1999 | Beams et al. | |
| 5,994,391 A | 11/1999 | Lee et al. | 514/431 |
| 6,344,483 B1 * | 2/2002 | Hallinan et al. | |

FOREIGN PATENT DOCUMENTS

| | | | |
|---|---|---|---|
| JP | 521471 | 6/1992 | C07D/239/42 |
| WO | WO 9313055 | 7/1993 | C07C/257/14 |
| WO | WO 9316055 | 8/1993 | C07D/281/10 |
| WO | WO 9525717 | 9/1995 | C07C/257/14 |
| WO | WO 9706802 | 2/1997 | A71K/31/495 |
| WO | WO 9946240 | 9/1999 | C07C/257/14 |
| WO | WO 0024719 | 5/2000 | C07D/237/14 |

OTHER PUBLICATIONS

Moussebois et al, Etudes des Proprietes Chimiques D'oxadiazoes–1,2,4 en Relation avec Leur Degre D'aromaticite, Moussebois et al Helvetica Chimica Acta, 1964, 47(3), pp. 838–848.*
Misko, et al., *European Journal of Pharmacology*; 233: 119–125 (1993).
Moncada, S. & Higgs, E., *FASEB Journal*; 9: 1319–1330 (1995).
Lee, et al, *Bioorganic Med. Chemistry*; 7(6): 1097–1104 (1999).
Young et al., *Bioorganic Med. Chemistry Letters*; 10(6): 597–600 (2000).
Greene, Theodora & Wuts, Peter. *Protective Groups in Organic Synthesis*, 3rd Edit.; John Wiley & Sons, New York, (1999), pp. 494–653.
Seebach, D. & Fadel, A., *Helvetica Chimica Acta*; 68: 1243 (1985).
Sasaki, A. & Brecias, E., *Tetrahedron Letters*; 21(44): 4263–4264 (1980).
O'Donnell, M. & Polt, R., *Journal of Organic Chemistry*; 47: 2663 (1982).
Moussebois, C. & Eloy, F., *Helvetica Chimica Acta*; 19: 838–848 (1964).
Bernando, et al., *Inorganic Chemistry*; 35(2): 387–396 (1996).
Bredt & Snyder, *Proceedings of the National Academy of Science USA*; 87: 682–685 (1990).
Moore et al., *Journal of Medicinal Chemistry*; 39(3): 669–672 (1996).
Rodi et al., *The Biology of Nitric Oxide, Part 4: Enzymology, Biochemistry, & Immunology*; Moncada, S; Freelisch, M; Busse, R; Higgs, E, Eds.; Portland Press Ltd., London, (1995) pp 447–450.
Misko, et al., *Analytical Biochemistry*; 214(1): 11–16 (1993).
Wright, W B et al, Journal of Medicinal Chemistry., vol. 29, No. 4, 1986, pp. 523–530, American Chemical Society., US Issn: 0022–2623.
Mindl, J et al, Tetrahedron Letters., vol. 26, No. 26, 1995, pp. 4471–4474, Elsevier Science Publishers, Amsterdam., NL Issn: 0040–4039.

* cited by examiner

*Primary Examiner*—Johann R. Richter
*Assistant Examiner*—Paul A. Zucker
(74) *Attorney, Agent, or Firm*—Philip B. Pelster, II

(57) ABSTRACT

The present invention relates to 2-amino-2-alkyl-4 hexenoic and hexynoic acid derivatives and their use in therapy, in particular their use as nitric oxide synthase inhibitors.

204 Claims, No Drawings

2-AMINO-2-ALKYL-4 HEXENOIC AND HEXYNOIC ACID DERIVATIVES USEFUL AS NITRIC OXIDE SYNTHASE INHIBITORS

CROSS REFERENCE TO RELATED APPLICATIONS

This application claims the benefit of U.S. Provisional Application Serial No. 60/232,680, filed Sep. 15, 2000.

FIELD OF THE INVENTION

The present invention relates to 2-amino-2-alkyl-4 hexenoic and hexynoic acid derivatives and their use in therapy, in particular their use as nitric oxide synthase inhibitors.

RELATED ART

It has been known since the early 1980's that the vascular relaxation caused by acetylcholine is dependent on the vascular endothelium. The endothelium-derived relaxing factor (EDRF), now known to be nitric oxide (NO) is generated in the vascular endothelium by nitric oxide synthase (NOS). The activity of NO as a vasodilator has been known for well over 100 years. In addition, NO is the active species deriving from amylnitrite, glyceryltrinitrate and other nitrovasodilators. The identification of EDRF as NO has coincided with the discovery of a biochemical pathway by which NO is synthesized from the amino acid L-arginine by the enzyme NO synthase.

Nitric oxide is an endogenous stimulator of the soluble guanylate cyclase. In addition to endothelium-dependent relaxation, NO is involved in a number of biological actions including cytotoxicity of phagocytic cells and cell-to-cell communication in the central nervous system.

There are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed, this inducible nitric oxide synthase (hereinafter "iNOS") generates NO continuously for long periods.

The NO released by each of the two constitutive enzymes acts as a transduction mechanism underlying several physiological responses. The NO produced by the inducible enzyme is a cytotoxic molecule for tumor cells and invading microorganisms. It also appears that adverse effects of excess NO production, in particular pathological vasodilation and tissue damage, may result largely from the NO synthesized by iNOS.

There is a growing body of evidence that NO may be involved in the degeneration of cartilage which takes place as a result of certain conditions such as arthritis and it is also known that NO synthesis is increased in rheumatoid arthritis and in osteoarthritis.

Some of the NO synthase inhibitors proposed for therapeutic use are non-selective; they inhibit both the constitutive and the inducible NO synthases. Use of such a non-selective NO synthase inhibitor requires that great care be taken in order to avoid the potentially serious consequences of over-inhibition of the constitutive NO-synthase, such consequences including hypertension and possible thrombosis and tissue damage. In particular, in the case of the therapeutic use of L-NMMA (a non-selective NO synthase inhibitor) for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use (S. Moncada and E. Higgs, FASEB J., 9, 1319–1330, 1995).

PCT International Publication No. WO 93/13055 and U.S. Pat. No. 5,132,453, the disclosure of which are hereby incorporated by reference in their entirety as if written herein, disclose compounds that inhibit nitric oxide synthesis and preferentially inhibit the inducible isoform of nitric oxide synthase.

PCT International Publication No. WO 95/25717 discloses certain amidino derivatives as being useful in inhibiting inducible nitric oxide synthase.

Various attempts have been made to improve the potency and selectivity of NOS inhibitors by adding one or more rigidifying elements to the inhibitor's structure. Publications by Y. Lee et al (*Bioorg. Med. Chem.* 7, 1097 (1999)) and R. J. Young et al (*Bioorg. Med. Chem. Lett.* 10, 597 (2000)) teach that imposing conformational rigidity with one or more carbon-carbon double bonds is not a favorable approach to impart selectivity for NOS inhibitors.

SUMMARY OF THE INVENTION

Compounds have now been found which have the advantage of being very efficacious in the human cartilage explant assay, a model for osteoarthritis.

The present invention demonstrates that a carbon-carbon double bond can be used as a rigidifying element, and the resulting compounds have unexpected potency and selectivity for inhibition of inducible NOS.

The present invention demonstrates that a carbon-carbon double bond imparts a favorable interaction with inducible NOS, such that the resulting compounds have unexpected potency and selectivity for inhibition of inducible NOS over the constitutive isoforms.

Further, compounds of the present invention have the advantage of being very efficacious as iNOS inhibitors in the human cartilage explant assay, a model for osteoarthritis. At the same time the compounds of the present invention are surprisingly less able to penetrate certain non-target organs in test systems, especially in comparison to the compounds of WO 93/13055. This surprising differentiation in expected access between the target organ (cartilage) and other organs is an unexpected advantage for the compounds of the present invention.

In a broad aspect, compounds of the present invention are represented by:

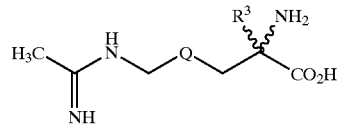

-continued

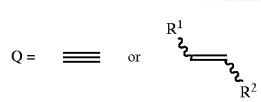

or a pharmaceutically acceptable salt thereof, wherein:
R$^1$ is selected from the group consisting of hydrogen, halo, $C_1$–$C_5$ alkyl and $C_1$–$C_5$ alkyl substituted by alkoxy or one or more halo;
R$^2$ is selected from the group consisting of hydrogen, halo, $C_1$–$C_5$ alkyl and $C_1$–$C_5$ alkyl substituted by alkoxy or one or more halo;
R$^3$ is $C_1$–$C_5$ alkyl or $C_1$–$C_5$ alkyl be substituted by alkoxy or one or more halo.

In an embodiment represented by Formula I, the invention relates to:

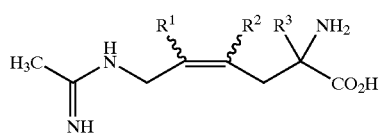

or a pharmaceutically acceptable salt thereof, wherein:
R$^1$ is selected from the group consisting of hydrogen, halo, $C^1$-$C_5$ alkyl and $C_1$–$C^5$ alkyl substituted by alkoxy or one or more halo;
R$^2$ is selected from the group consisting of hydrogen, halo, $C_1$–$C_5$ alkyl and $C_1$–$C^5$ alkyl substituted by alkoxy or one or more halo;
R$^3$ is $C_1$–$C_5$ alkyl or $C_1$–$C_5$ alkyl substituted by alkoxy or one or more halo.

In an embodiment represented by Formula II, the invention relates to:

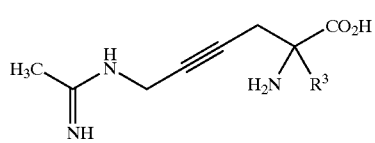

or a pharmaceutically acceptable salt thereof, wherein:
R$^3$ is $C_1$–$C_5$ alkyl, said $C_1$–$C_5$ alkyl optionally substituted by halo or alkoxy, said alkoxy optionally substituted by one or more halo.

In an embodiment represented by Formula III, the invention relates to:

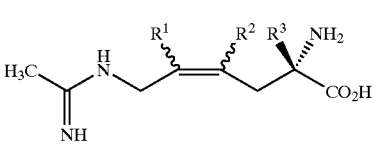

or a pharmaceutically acceptable salt thereof, wherein:
R$^1$ is selected from the group consisting of hydrogen, halo, $C_1$–$C_5$ alkyl and $C_1$–$C_5$ alkyl substituted by alkoxy or one or more halo;
R$^2$ is selected from the group consisting of hydrogen, halo, $C_1$–$C_5$ alkyl and $C_1$–$C_5$ alkyl substituted by alkoxy or one or more halo;
R$^3$ is $C_1$–$C_5$ alkyl or $C_1$–$C_5$ alkyl substituted by alkoxy or one or more halo.

In an embodiment represented by Formula V, the invention relates to:

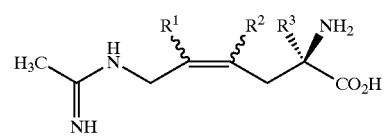

or a pharmaceutically acceptable salt thereof, wherein:
R$^1$ is selected from the group consisting of hydrogen, halo, $C_1$–$C_5$ alkyl and $C_1$–$C_5$ alkyl substituted by alkoxy or one or more halo;
R$^2$ is selected from the group consisting of hydrogen, halo, $C_1$–$C_5$ alkyl and $C_1$–$C_5$ alkyl substituted by alkoxy or one or more halo;
R$^3$ is $C_1$–$C_5$ alkyl or $C_1$–$C_5$ alkyl substituted by alkoxy or one or more halo.

In an embodiment represented by Formula IV, the invention relates to:

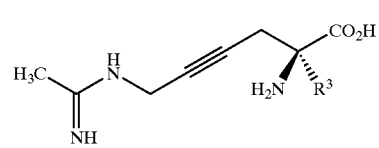

or a pharmaceutically acceptable salt thereof, wherein:
R$^3$ is $C_1$–$C_5$ alkyl or $C_1$–$C_5$ alkyl substituted by alkoxy or one or more halo.

In an embodiment represented by Formula V, the invention relates to:

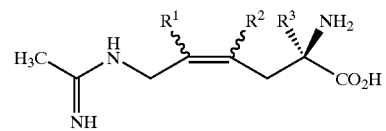

or a pharmaceutically acceptable salt thereof, wherein:
R$^1$ is selected from the group consisting of hydrogen, halo, $C_1$–$C_5$ alkyl and $C_1$–$C_5$ alkyl substituted by alkoxy or one or more halo;
R$^2$ is selected from the group consisting of hydrogen, halo, $C_1$–$C_5$ alkyl and $C_1$–$C_5$ alkyl substituted by alkoxy or one or more halo;
R$^3$ is $C_1$–$C_5$ alkyl or $C_1$–$C_5$ alkyl be substituted by alkoxy or one or more halo.

In an embodiment represented by Formula VI, the invention relates to:

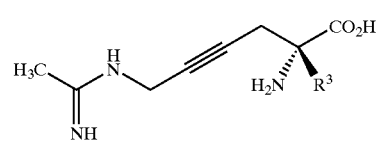

or a pharmaceutically acceptable salt thereof, wherein:
R$^3$ is $C_1$–$C_5$ alkyl or $C_1$–$C_5$ alkyl substituted by alkoxy or one or more halo.

In a broad aspect, the present invention is directed to novel compounds, pharmaceutical compositions, process for preparing novel compounds, process for preparing pharmaceutical compositions, and methods of using said compounds and compositions for inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering. The present compounds possess useful nitric oxide synthase inhibiting activity, and are expected to be useful in the treatment or prophylaxis of a disease or condition in which the synthesis or over-synthesis of nitric oxide forms a contributory part.

Compounds of the present invention will be useful for treating, among other things, inflammation in a subject, or for treating other nitric oxide synthase-mediated disorders, such as, as an analgesic in the treatment of pain and headaches. The compounds of the present invention will be useful in the treatment of pain including somatogenic (either nociceptive or neuropathic), both acute and chronic, and could be used in a situation including neuropathic pain for which a common NSAID, opioid analgesic or certain anticonvulsants would traditionally be administered.

Included within the scope of the present invention are novel intermediates useful for synthesizing compounds of the present invention.

Conditions in which the compounds of the present invention will provide an advantage in inhibiting NO production from L-arginine include arthritic conditions. For example, compounds of the present invention will be useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis.

Compounds of the invention will be further useful in the treatment of asthma, bronchitis, menstrual cramps (e.g., dysmenorrhea), premature labor, tendinitis, bursitis, skin-related conditions such as psoriasis, eczema, burns, sunburn, dermatitis, pancreatitis, hepatitis, and post-operative inflammation including inflammation from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis.

Compounds of the invention would be useful in treating inflammation and tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as glaucoma, retinitis, retinopathies, uveitis, ocular photophobia, and of inflammation and pain associated with acute injury to the eye tissue. Of particular interest among the uses of the present inventive compounds is the treatment of glaucoma, especially where symptoms of glaucoma are caused by the production of nitric oxide, such as in nitric oxide-mediated nerve damage. The compounds would also be useful in the treatment of pulmonary inflammation, such as that associated with viral infections and cystic fibrosis.

The compounds would also be useful for the treatment of certain central nervous system disorders, such as cortical dementias including Alzheimer's disease, and central nervous system damage resulting from stroke, ischemia and trauma. These compounds would also be useful in the treatment of allergic rhinitis, respiratory distress syndrome, endotoxin shock syndrome, and atherosclerosis. The compounds would also be useful in the treatment of pain, including but not limited to postoperative pain, dental pain, muscular pain, pain caused by temperoramandibular joint syndrome, and pain resulting from cancer. The compounds would be useful for the prevention of dementias, such as Alzheimer's disease.

Besides being useful for human treatment, these compounds are also useful for veterinary treatment of companion animals, exotic animals and farm animals, including mammals and other vertebrates. More preferred animals include horses, dogs, and cats.

The present compounds may also be used in co-therapies, partially or completely, in place of other conventional anti-inflammatory therapies, such as together with steroids, NSAIDs, COX-2 selective inhibitors, matrix metalloproteinase inhibitors, 5-lipoxygenase inhibitors, $LTB_4$ antagonists and $LTA_4$ hydrolase inhibitors.

Other conditions in which the compounds of the present invention will provide an advantage in inhibiting NO inhibition include cardiovascular ischemia, diabetes (type I or type II), congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (for example, secondary to cardiac arrest), multiple sclerosis and other central nervous system disorders mediated by NO, for example Parkinson's disease. Further neurodegenerative disorders in which NO inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia, such as, for example pre-senile dementia, and AIDS-related dementia, cachexia, Sydenham's chorea, Huntington's disease, Amyotrophic Lateral Sclerosis, Korsakoff's disease, imbecility relating to a cerebral vessel disorder, sleeping disorders, schizophrenia, depression, depression or other symptoms associated with Premenstrual Syndrome (PMS), anxiety and septic shock.

Still other disorders or conditions which will be advantageously treated by the compounds of the present invention include treatment of prevention of opiate tolerance in patients needing protracted opiate analgesics, and benzodiazepine tolerance in patients taking benzodiazepines, and other addictive behavior, for example, nicotine addiction, alcoholism, and eating disorders. The compounds and methods of the present invention will also be useful in the treatment or prevention of drug withdrawal symptoms, for example treatment or prevention of symptoms of withdrawal from opiate, alcohol, or tobacco addiction. The present inventive compounds may also be useful to prevent tissue damage when therapeutically combined with antibacterial or antiviral agents.

The compounds of the present invention will also be useful in inhibiting NO production from L-arginine including systemic hypotension associated with septic and/or toxic hemorrhagic shock induced by a wide variety of agents; therapy with cytokines such as TNF, IL-1 and IL-2; and as an adjuvant to short term immunosuppression in transplant therapy.

Compounds of the invention are useful for the prevention or treatment of cancer, such as colorectal cancer, and cancer of the breast, lung, prostate, bladder, cervix and skin. The present invention is further directed to the use of the compounds of the present invention for the treatment and prevention of neoplasias. The neoplasias that will be treatable or preventable by the compounds and methods of the present invention include brain cancer, bone cancer, a leukemia, such as, for example chronic lymphocytic leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, urogenital cancers, such as ovary cancer, cervical cancer, vulvar cancer, and lung cancer, breast cancer and skin cancer, such as squamous cell, melanoma, and basal cell cancers, prostate cancer, renal cell carcinoma, and other known cancers that effect epithelial cells throughout the body. Compounds of the present invention will be effective as well for treatment of mesenchymal derived neoplasias. Preferably, the neoplasia to be treated is selected from gastrointestinal cancer, liver cancer, bladder cancer, pancreas cancer, ovary cancer, prostate cancer, cervical cancer, vulvar cancer, lung cancer, breast cancer and skin cancer, such as squamous cell and basal cell cancers. The present compounds and methods can also be used to treat the fibrosis which occurs with radiation therapy. The present compounds and methods can be used to treat subjects having adenomatous polyps, including those with familial adenomatous polyposis (FAP). Additionally, the present compounds and methods can be used to prevent polyps from forming in patients at risk of FAP.

Conjunctive treatment of a compound of the present invention with another antineoplastic agent will produce a synergistic effect or alternatively reduce the toxic side effects associated with chemotherapy by reducing the therapeutic dose of the side effect-causing agent needed for therapeutic efficacy or by directly reducing symptoms of toxic side effects caused by the side effect-causing agent. A compound of the present invention will further be useful as an adjunct to radiation therapy to reduce side effects or enhance efficacy. In the present invention, another agent which can be combined therapeutically with a compound of the present invention includes any therapeutic agent which is capable of inhibiting the enzyme cyclooxygenase-2 ("COX-2"). Preferably such COX-2 inhibiting agents inhibit COX-2 selectively relative to the enzyme cyclooxygenase-1 ("COX-1"). Such a COX-2 inhibitor is known as a "COX-2 selective inhibitor". More preferably, a compound of the present invention can be therapeutically combined with a COX-2 selective inhibitor wherein the COX-2 selective inhibitor selectively inhibits COX-2 at a ratio of at least 10:1 relative to inhibition of COX-1, more preferably at least 30:1, and still more preferably at least 50:1 in an in vitro test. COX-2 selective inhibitors useful in therapeutic combination with the compounds of the present invention include celecoxib, valdecoxib, deracoxib, etoricoxib, rofecoxib, ABT-963 (2-(3,4-difluorophenyl)-4-(3-hydroxy-3-methyl-1-butoxy)-5-[4-(methylsulfonyl)phenyl-3(2H)-pyridazinone; described in PCT Patent Application No. WO 00/24719), or meloxicam. A compound of the present invention can also be advantageously used in therapeutic combination with a prodrug of a COX-2 selective inhibitor, for example parecoxib.

Another chemotherapeutic agent which will be useful in combination with a compound of the present invention can be selected, for example, from the following non-comprehensive and non-limiting list:

Alpha-difluoromethylornithine (DFMO), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, uroguanylin, combretastatin, dolastatin, idarubicin, epirubicin, estramustine, cyclophosphamide, 9-amino-2-(S)-camptothecin, topotecan, irinotecan (Camptosar), exemestane, decapeptyl (tryptorelin), or an omega-3 fatty acid.

Examples of radioprotective agents which may be used in a combination therapy with the compounds of this invention include AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

The compounds of the present invention will also be useful in treatment or prevention of angiogenesis-related disorders or conditions, for example, tumor growth, metastasis, macular degeneration, and atherosclerosis.

In a further embodiment, the present invention also provides therapeutic combinations for the treatment or prevention of ophthalmic disorders or conditions such as glaucoma. For example the present inventive compounds advantageously will be used in therapeutic combination with a drug which reduces the intraocular pressure of patients afflicted with glaucoma. Such intraocular pressure-reducing drugs include without limitation; latanoprost, travoprost, bimatoprost, or unoprostol. The therapeutic combination of a compound of the present invention plus an intraocular pressure-reducing drug will be useful because each is believed to achieve its effects by affecting a different mechanism.

In another combination of the present invention, the present inventive compounds can be used in therapeutic combination with an antihyperlipidemic or cholesterol-lowering drug such as a benzothiepine or a benzothiazepine antihyperlipidemic drug. Examples of benzothiepine antihyperlipidemic drugs useful in the present inventive therapeutic combination can be found in U.S. Pat. No. 5,994,391, herein incorporated by reference. Some benzothiazepine antihyperlipidemic drugs are described in WO 93/16055. Alternatively, the antihyperlipidemic or cholesterol-lowering drug useful in combination with a compound of the present invention can be an HMG Co-A reductase inhibitor. Examples of HMG Co-A reductase inhibitors useful in the present therapeutic combination include, individually, benfluorex, fluvastatin, lovastatin, provastatin, simvastatin, atorvastatin, cerivastatin, bervastatin, ZD-9720 (described in PCT Patent Application No. WO 97/06802), ZD-4522 (CAS No. 147098-20-2 for the calcium salt; CAS No. 147098-18-8 for the sodium salt; described in European Patent No. EP 521471), BMS 180431 (CAS No. 129829-03-4), or NK-104 (CAS No. 141750-63-2). The therapeutic combination of a compound of the present invention plus an antihyperlipidemic or cholesterol-lowering drug will be useful, for example, in reducing the risk of formation of atherosclerotic lesions in blood vessels. For example, atherosclerotic lesions often initiate at inflamed sites in blood vessels. It is established that antihyperlipidemic or cholesterol-lowering drug reduce risk of formation of atherosclerotic lesions by lowering lipid levels in blood. Without limiting the invention to a single mechanism of action, it is believed that one way the compounds of the present combination will work in concert to provide improved control of atherosclerotic lesions by, for example, reducing inflammation of the blood vessels in concert with lowering blood lipid levels.

In another embodiment of the invention, the present compounds can be used in combination with other compounds or therapies for the treatment of central nervous conditions or disorders such as migraine. For example, the present compounds can be used in therapeutic combination with caffeine, a 5-HT-1B/1D agonist (for example, a triptan such as sumatriptan, naratriptan, zolmitriptan, rizatriptan, almotriptan, or frovatriptan), a dopamine D4 antagonist (e.g., sonepiprazole), aspirin, acetaminophen, ibuprofen, indomethacin, naproxen sodium, isometheptene, dichloralphenazone, butalbital, an ergot alkaloid (e.g., ergotamine, dihydroergotamine, bromocriptine, ergonovine, or methyl ergonovine), a tricyclic antidepressant (e.g., amitriptyline or nortriptyline), a serotonergic antagonist (e.g., methysergide or cyproheptadine), a beta-andrenergic antagonist (e.g., propranolol, timolol, atenolol, nadolol, or metprolol), or a monoamine oxidase inhbitor (e.g., phenelzine or isocarboxazid).

A further embodiment provides a therapeutic combination of a compound of the present invention with an opioid compound. Opioid compounds useful in this combination include without limitation morphine, methadone, hydromorphone, oxymorphone, levorphanol, levallorphan, codeine, dihydrocodeine, dihydrohydroxycodeinone, pentazocine, hydrocodone, oxycodone, nalmefene, etorphine, levorphanol, fentanyl, sufentanil, DAMGO, butorphanol, buprenorphine, naloxone, naltrexone, CTOP, diprenorphine, beta-funaltrexamine, naloxonazine, nalorphine, pentazocine, nalbuphine, naloxone benzoylhydrazone, bremazocine, ethylketocyclazocine, U50,488, U69,593, spiradoline, nor-binaltorphimine, naltrindole, DPDPE, [D-la$^2$, glu$^4$]deltorphin, DSLET, met-enkephalin, leu-enkaphalin, beta-endorphin, dynorphin A, dynorphin B, and alpha-neoendorphin. An advantage to the combination of the present invention with an opioid compound is that the present inventive compounds will allow a reduction in the dose of the opioid compound, thereby reducing the risk or severity of opioid side effects, such as opioid addiction.

DETAILED DESCRIPTION OF THE INVENTION

In a broad aspect, compounds of the present invention are represented by:

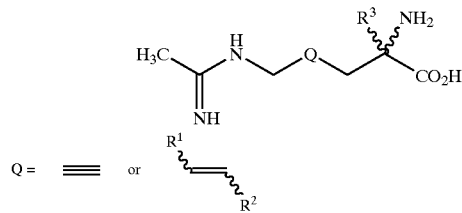

or a pharmaceutically acceptable salt thereof, wherein:
  $R^1$ is selected from the group consisting of hydrogen, halo, $C_1$–$C_5$ alkyl and $C_1$–$C_5$ alkyl substituted by alkoxy or one or more halo;
  $R^2$ is selected from the group consisting of hydrogen, halo, $C_1$–$C_5$ alkyl and $C_1$–$C_5$ alkyl substituted by alkoxy or one or more halo;
  $R^3$ is $C_1$–$C_5$ alkyl or $C_1$–$C_5$ alkyl be substituted by alkoxy or one or more halo.

In an embodiment represented by Formula I, the invention relates to:

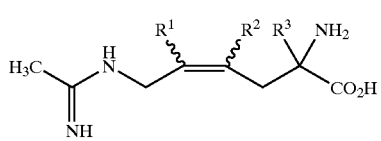

I or a pharmaceutically acceptable salt thereof, wherein:
  $R_1$ is selected from the group consisting of hydrogen, halo, $C_1$–$C_5$ alkyl and $C_1$–$C_5$ alkyl substituted by alkoxy or one or more halo;

$R^2$ is selected from the group consisting of hydrogen, halo, $C_1$–$C_5$ alkyl and $C_1$–$C_5$ alkyl substituted by alkoxy or one or more halo;
  $R^3$ is $C_1$–$C_5$ alkyl or $C_1$–$C_5$ alkyl substituted by alkoxy or one or more halo.

In one embodiment of the present invention represented by Formula I, the compound is the Z isomer.

In another embodiment of the present invention represented by Formula I, the compound is the E isomer.

In yet another embodiment of the present invention represented by Formula I, $R^1$ is hydrogen, halo, or $C_1$–$C_5$ alkyl, said $C_1$–$C_5$ alkyl optionally substituted by halo or alkoxy, said alkoxy optionally substituted by one or more halo; $R^2$ is hydrogen, halo or $C_1$–$C_5$ alkyl, said $C_1$–$C_5$ alkyl optionally substituted by halo or alkoxy, said alkoxy optionally substituted by one or more halo; and $R^3$ is $C_1$–$C_5$ alkyl, said $C_1$–$C_5$ alkyl optionally substituted by halo or alkoxy.

In another embodiment of the present invention represented by Formula I, $R^1$ is hydrogen, halo, or $C_1$–$C_3$ alkyl; $R^2$ is hydrogen, halo or $C_1$–$C_3$ alkyl; and $R^3$ is $C_1$–$C_5$ alkyl, said $C_1$–$C_5$ alkyl optionally substituted by fluorine or alkoxy.

In a further embodiment of the present invention represented by Formula I, $R^1$ is hydrogen, halo, or $C_1$–$C_3$ alkyl; $R^2$ is hydrogen, halo or $C_1$–$C_3$ alkyl; and $R^3$ is $C_1$–$C_3$ alkyl.

In another embodiment of the present invention represented by Formula I, $R^1$ is hydrogen; $R^2$ is hydrogen, halo or $C_1$–$C_3$ alkyl; and $R^3$ is $C_1$–$C_3$ alkyl.

In a still further embodiment of the present invention represented by Formula I, $R^1$ is hydrogen; $R^2$ is hydrogen or halo; and $R^3$ is $C_1$–$C_3$ alkyl.

In another embodiment of the present invention represented by Formula I, $R^1$ is hydrogen; $R^2$ is hydrogen or fluorine; and $R^3$ is $C_1$–$C_3$ alkyl.

In another embodiment of the present invention represented by Formula I, $R^1$ is hydrogen; $R^2$ is hydrogen or fluorine; and $R^3$ is methyl.

In another embodiment of the present invention represented by Formula I, $R^1$ is hydrogen; $R^2$ is hydrogen; and $R^3$ is methyl.

In a further embodiment of the present invention represented by Formula I, $R^1$ is hydrogen; $R^2$ is fluorine; and $R^3$ is methyl.

In another embodiment of the present invention represented by Formula I, $R^1$ is halo; $R^2$ is hydrogen, halo or $C_1$–$C_3$ alkyl; and $R^3$ is $C_1$–$C_3$ alkyl.

In a further embodiment of the present invention represented by Formula I, $R^1$ is halo; $R^2$ is halo; and $R^3$ is $C_1$–$C_3$ alkyl.

In another embodiment of the present invention represented by Formula I, $R^1$ is fluorine; $R^2$ is fluorine; and $R^3$ is methyl.

In another embodiment of the present invention represented by Formula I, $R^1$ is fluorine; $R^2$ is hydrogen or $C_1$–$C_3$ alkyl; and $R^3$ is methyl.

In a further embodiment of the present invention represented by Formula I, $R^1$ is fluorine; $R^2$ is hydrogen; and $R^3$ is methyl.

In another embodiment of the present invention represented by Formula I, $R^1$ is methyl; $R^2$ is hydrogen; and $R^3$ is methyl.

In a further embodiment of the present invention represented by Formula I, $R^1$ is hydrogen; $R^2$ is methyl; and $R^3$ is methyl.

In another embodiment of the present invention represented by Formula I, $R^1$ is methyl; $R^2$ is methyl; and $R^3$ is methyl.

In yet another embodiment of the present invention represented by Formula I,: $R^1$ is hydrogen, halo or $C_1-C_5$ alkyl, said $C_1-C_5$ alkyl optionally substituted by alkoxy or one or more fluorine; $R^2$ is hydrogen, halo or $C_1-C_5$ alkyl, said $C_1-C_5$ alkyl optionally substituted by alkoxy or one or more fluorine; and $R^3$ is methyl optionally substituted by one or more alkoxy or halo.

In a further embodiment of the present invention represented by Formula I, $R^1$ is hydrogen or fluorine; $R^2$ is $C_1-C_3$ alkyl substituted by one or more halo; and $R^3$ is methyl.

In another embodiment of the present invention represented by Formula I, $R^1$ is hydrogen; $R^2$ is $CH_2F$; and $R^3$ is methyl.

In still another embodiment of the present invention represented by Formula I, $R^1$ is $CH_2F$; $R^2$ is hydrogen; and $R^3$ is methyl.

In a further embodiment of the present invention represented by Formula I, $R^1$ is hydrogen; $R^2$ is hydrogen; and $R^3$ is $CH_2F$.

In another embodiment of the present invention represented by Formula I, $R^1$ is hydrogen; $R^2$ is methoxymethyl; and $R^3$ is methyl.

In a further embodiment of the present invention represented by Formula I, $R^1$ is methoxymethyl; $R^2$ is hydrogen; and $R^3$ is methyl.

In another embodiment of the present invention represented by Formula I, $R^1$ is hydrogen; $R^2$ is hydrogen; and $R^3$ is methoxymethyl.

In an embodiment represented by Formula II, the invention relates to:

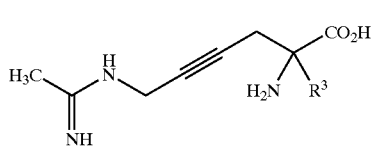

II or a pharmaceutically acceptable salt thereof, wherein:

$R^3$ is $C_1-C_5$ alkyl, said $C_1-C_5$ alkyl optionally substituted by halo or alkoxy, said alkoxy optionally substituted by one or more halo.

In another embodiment of the present invention represented by Formula II, $R^3$ is $C_1-C_5$ alkyl substituted by one or more halo.

In a further embodiment of the present invention represented by Formula II, $R^3$ is $C_1-C_5$ alkyl substituted by one or more fluorine.

In still another embodiment of the present invention represented by Formula II, $R^3$ is methyl substituted by one or more halo.

In yet another embodiment of the present invention represented by Formula II, $R^3$ is methyl substituted by one or more fluorine. In another embodiment of the present invention represented by Formula II, $R^3$ is $CH_2F$.

In still another embodiment of the present invention represented by Formula II, $R^3$ is $C_1-C_5$ alkyl substituted by alkoxy.

In a further embodiment of the present invention represented by Formula II, $R^3$ is methoxy methyl.

In yet another embodiment of the present invention represented by Formula II, $R^3$ is $C_1-C_5$ alkyl.

In another embodiment of the present invention represented by Formula II, $R^3$ is methyl.

In an embodiment represented by Formula III, the invention relates to:

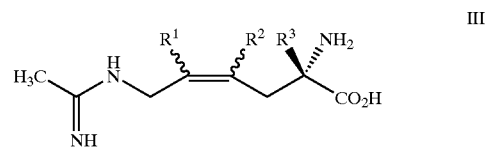

III or a pharmaceutically acceptable salt thereof, wherein:

$R_1$ is selected from the group consisting of hydrogen, halo, $C_1-C_5$ alkyl and $C_1-C_5$ alkyl substituted by alkoxy or one or more halo;

$R^2$ is selected from the group consisting of hydrogen, halo, $C_1-C_5$ alkyl and $C_1-C_5$ alkyl substituted by alkoxy or one or more halo;

$R^3$ is $C_1-C_5$ alkyl or $C_1-C_5$ alkyl substituted by alkoxy or one or more halo.

In one embodiment of the present invention represented by Formula III, the compound is the Z isomer.

In another embodiment of the present invention represented by Formula III, the compound is the E isomer.

In yet another embodiment of the present invention represented by Formula III, $R^1$ is hydrogen, halo, or $C_1-C_5$ alkyl, said $C_1-C_5$ alkyl optionally substituted by halo or alkoxy, said alkoxy optionally substituted by one or more halo; $R^2$ is hydrogen, halo or $C_1-C_5$ alkyl, said $C_1-C_5$ alkyl optionally substituted by halo or alkoxy, said alkoxy optionally substituted by one or more halo; and $R^3$ is $C_1-C_5$ alkyl, said $C_1-C_5$ alkyl optionally substituted by halo or alkoxy.

In another embodiment of the present invention represented by Formula III, $R^1$ is hydrogen, halo, or $C_1-C_3$ alkyl; $R^2$ is hydrogen, halo or $C_1-C_3$ alkyl; and $R^3$ is $C_1-C_5$ alkyl, said $C_1-C_5$ alkyl optionally substituted by fluorine or alkoxy.

In a further embodiment of the present invention represented by Formula III, $R^1$ is hydrogen, halo, or $C_1-C_3$ alkyl; $R^2$ is hydrogen, halo or $C_1-C_3$ alkyl; and $R^3$ is $C_1-C_3$ alkyl.

In another embodiment of the present invention represented by Formula III, $R^1$ is hydrogen; $R^2$ is hydrogen, halo or $C_1-C_3$ alkyl; and $R^3$ is $C_1-C_3$ alkyl.

In a still further embodiment of the present invention represented by Formula III, $R^1$ is hydrogen; $R^2$ is hydrogen or halo; and $R^3$ is $C_1-C_3$ alkyl.

In another embodiment of the present invention represented by Formula III, $R^1$ is hydrogen; $R^2$ is hydrogen or fluorine; and $R^3$ is $C_1-C_3$ alkyl.

In another embodiment of the present invention represented by Formula III, $R^1$ is hydrogen; $R^2$ is hydrogen or fluorine; and $R^3$ is methyl.

In another embodiment of the present invention represented by Formula III, $R^1$ is hydrogen; $R^2$ is hydrogen; and $R^3$ is methyl.

In a further embodiment of the present invention represented by Formula III, $R^1$ is hydrogen; $R^2$ is fluorine; and $R^3$ is methyl.

In another embodiment of the present invention represented by Formula III, $R^1$ is halo; $R^2$ is hydrogen, halo or $C_1-C_3$ alkyl; and $R^3$ is $C_1-C_3$ alkyl.

In a further embodiment of the present invention represented by Formula III, $R^1$ is halo; $R^2$ is halo; and $R^3$ is $C_1-C_3$ alkyl.

In another embodiment of the present invention represented by Formula III, $R^1$ is fluorine; $R^2$ is fluorine; and $R^3$ is methyl.

In another embodiment of the present invention represented by Formula III, $R^1$ is fluorine; $R^2$ is hydrogen or $C_1-C_3$ alkyl; and $R^3$ is methyl.

In a further embodiment of the present invention represented by Formula III, $R^1$ is fluorine; $R^2$ is hydrogen; and $R^3$ is methyl.

In another embodiment of the present invention represented by Formula III, $R^1$ is methyl; $R^2$ is hydrogen; and $R^3$ is methyl.

In a further embodiment of the present invention represented by Formula III, $R^1$ is hydrogen; $R^2$ is methyl; and $R^3$ is methyl.

In another embodiment of the present invention represented by Formula III, $R^1$ is methyl; $R^2$ is methyl; and $R^3$ is methyl.

In yet another embodiment of the present invention represented by Formula III,: $R^1$ is hydrogen, halo or $C_1$–$C_5$ alkyl, said $C_1$–$C_5$ alkyl optionally substituted by alkoxy or one or more fluorine; $R^2$ is hydrogen, halo or $C_1$–$C_5$ alkyl, said $C_1$–$C_5$ alkyl optionally substituted by alkoxy or one or more fluorine; and $R^3$ is methyl optionally substituted by one or more alkoxy or halo.

In a further embodiment of the present invention represented by Formula III, $R^1$ is hydrogen or fluorine; $R^2$ is $C_1$–$C_3$ alkyl substituted by one or more halo; and $R^3$ is methyl.

In another embodiment of the present invention represented by Formula III, $R^1$ is hydrogen; $R^2$ is $CH_2F$; and $R^3$ is methyl.

In still another embodiment of the present invention represented by Formula III, $R^1$ is $CH_2F$; $R^2$ is hydrogen; and $R^3$ is methyl.

In a further embodiment of the present invention represented by Formula III, $R^1$ is hydrogen; $R^2$ is hydrogen; and $R^3$ is $CH_2F$.

In another embodiment of the present invention represented by Formula III, $R^1$ is hydrogen; $R^2$ is methoxymethyl; and $R^3$ is methyl.

In a further embodiment of the present invention represented by Formula III, $R^1$ is methoxymethyl; $R^2$ is hydrogen; and $R^3$ is methyl.

In another embodiment of the present invention represented by Formula III, $R^1$ is hydrogen; $R^2$ is hydrogen; and $R^3$ is methoxymethyl.

In an embodiment represented by Formula IV, the invention relates to:

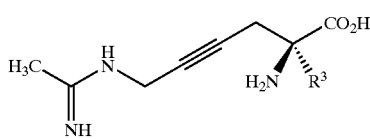

or a pharmaceutically acceptable salt thereof, wherein:
$R^3$ is $C_1$–$C_5$ alkyl or $C_1$–$C_5$ alkyl substituted by alkoxy or one or more halo.

In another embodiment of the present invention represented by Formula II, $R^3$ is $C_1$–$C_5$ alkyl substituted by one or more halo.

In a further embodiment of the present invention represented by Formula II, $R^3$ is $C_1$–$C_5$ alkyl substituted by one or more fluorine.

In still another embodiment of the present invention represented by Formula II, $R^3$ is methyl substituted by one or more halo.

In yet another embodiment of the present invention represented by Formula II, $R^3$ is methyl substituted by one or more fluorine. In another embodiment of the present invention represented by Formula II, $R^3$ is $CH_2F$.

In still another embodiment of the present invention represented by Formula II, $R^3$ is $C_1$–$C_5$ alkyl substituted by alkoxy.

In a further embodiment of the present invention represented by Formula II, $R^3$ is methoxy methyl.

In yet another embodiment of the present invention represented by Formula II, $R^3$ is $C_1$–$C_5$ alkyl.

In another embodiment of the present invention represented by Formula II, $R^3$ is methyl.

In an embodiment represented by Formula V, the invention relates to:

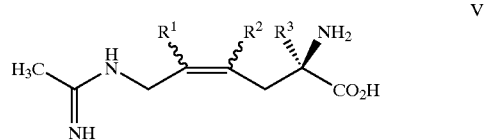

or a pharmaceutically acceptable salt thereof, wherein:
$R^1$ is selected from the group consisting of hydrogen, halo, $C_1$–$C_5$ alkyl and $C_1$–$C_5$ alkyl substituted by alkoxy or one or more halo;
$R^2$ is selected from the group consisting of hydrogen, halo, $C_1$–$C_5$ alkyl and $C_1$–$C_5$ alkyl substituted by alkoxy or one or more halo;
$R^3$ is $C_1$–$C_5$ alkyl or $C_1$–$C_5$ alkyl substituted by alkoxy or one or more halo.

In one embodiment of the present invention represented by Formula V, the compound is the Z isomer.

In another embodiment of the present invention represented by Formula V, the compound is the E isomer.

In yet another embodiment of the present invention represented by Formula V, $R^1$ is hydrogen, halo, or $C_1$–$C_5$ alkyl, said $C_1$–$C_5$ alkyl optionally substituted by halo or alkoxy, said alkoxy optionally substituted by one or more halo; $R^2$ is hydrogen, halo or $C_1$–$C_5$ alkyl, said $C_1$–$C_5$ alkyl optionally substituted by halo or alkoxy, said alkoxy optionally substituted by one or more halo; and $R^3$ is $C_1$–$C_5$ alkyl, said $C_1$–$C_5$ alkyl optionally substituted by halo or alkoxy.

In another embodiment of the present invention represented by Formula V, $R^1$ is hydrogen, halo, or $C_1$–$C_3$ alkyl; $R^2$ is hydrogen, halo or $C_1$–$C_3$ alkyl; and $R^3$ is $C_1$–$C_5$ alkyl, said $C_1$–$C_5$ alkyl optionally substituted by fluorine or alkoxy.

In a further embodiment of the present invention represented by Formula V, $R^1$ is hydrogen, halo, or $C_1$–$C_3$ alkyl; $R^2$ is hydrogen, halo or $C_1$–$C_3$ alkyl; and $R^3$ is $C_1$–$C_3$ alkyl.

In another embodiment of the present invention represented by Formula V, $R^1$ is hydrogen; $R^2$ is hydrogen, halo or $C_1$–$C_3$ alkyl; and $R^3$ is $C_1$–$C_3$ alkyl.

In a still further embodiment of the present invention represented by Formula V, $R^1$ is hydrogen; $R^2$ is hydrogen or halo; and $R^3$ is $C_1$–$C_3$ alkyl.

In another embodiment of the present invention represented by Formula V, $R^1$ is hydrogen; $R^2$ is hydrogen or fluorine; and $R^3$ is $C_1$–$C_3$ alkyl.

In another embodiment of the present invention represented by Formula V, $R^1$ is hydrogen; $R^2$ is hydrogen or fluorine; and $R^3$ is methyl.

In another embodiment of the present invention represented by Formula V, $R^1$ is hydrogen; $R^2$ is hydrogen; and $R^3$ is methyl.

In a further embodiment of the present invention represented by Formula V, $R^1$ is hydrogen; $R^2$ is fluorine; and $R^3$ is methyl.

In another embodiment of the present invention represented by Formula V, $R^1$ is halo; $R^2$ is hydrogen, halo or $C_1$–$C_3$ alkyl; and $R^3$ is $C_1$–$C_3$ alkyl.

In a further embodiment of the present invention represented by Formula V, $R^1$ is halo; $R^2$ is halo; and $R^3$ is $C_1$–$C_3$ alkyl.

In another embodiment of the present invention represented by Formula V, $R^1$ is fluorine; $R^2$ is fluorine; and $R^3$ is methyl.

In another embodiment of the present invention represented by Formula V, $R^1$ is fluorine; $R^2$ is hydrogen or $C_1$–$C_3$ alkyl; and $R^3$ is methyl.

In a further embodiment of the present invention represented by Formula V, $R^1$ is fluorine; $R^2$ is hydrogen; and $R^3$ is methyl.

In another embodiment of the present invention represented by Formula V, $R^1$ is methyl; $R^2$ is hydrogen; and $R^3$ is methyl.

In a further embodiment of the present invention represented by Formula V, $R^1$ is hydrogen; $R^2$ is methyl; and $R^3$ is methyl.

In another embodiment of the present invention represented by Formula V, $R^1$ is methyl; $R^2$ is methyl; and $R^3$ is methyl.

In yet another embodiment of the present invention represented by Formula V,: $R^1$ is hydrogen, halo or $C_1$–$C_5$ alkyl, said $C_1$–$C_5$ alkyl optionally substituted by alkoxy or one or more fluorine; $R^2$ is hydrogen, halo or $C_1$–$C_5$ alkyl, said $C_1$–$C_5$ alkyl optionally substituted by alkoxy or one or more fluorine; and $R^3$ is methyl optionally substituted by one or more alkoxy or halo.

In a further embodiment of the present invention represented by Formula V, $R^1$ is hydrogen or fluorine; $R^2$ is $C_1$–$C_3$ alkyl substituted by one or more halo; and $R^3$ is methyl.

In another embodiment of the present invention represented by Formula V, $R^1$ is hydrogen; $R^2$ is $CH_2F$; and $R^3$ is methyl.

In still another embodiment of the present invention represented by Formula V, $R^1$ is $CH_2F$; $R^2$ is hydrogen; and $R^3$ is methyl.

In a further embodiment of the present invention represented by Formula V, $R^1$ is hydrogen; $R^2$ is hydrogen; and $R^3$ is $CH_2F$.

In another embodiment of the present invention represented by Formula V, $R^1$ is hydrogen; $R^2$ is methoxymethyl; and $R^3$ is methyl.

In a further embodiment of the present invention represented by Formula V, $R^1$ is methoxymethyl; $R^2$ is hydrogen; and $R^3$ is methyl.

In another embodiment of the present invention represented by Formula V, $R^1$ is hydrogen; $R^2$ is hydrogen; and $R^3$ is methoxymethyl.

In an embodiment represented by Formula VI, the invention relates to:

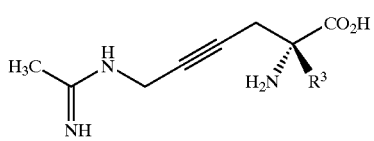

VI or a pharmaceutically acceptable salt thereof, wherein:
$R^3$ is $C_1$–$C_5$ alkyl or $C_1$–$C_5$ alkyl substituted by alkoxy or one or more halo.

In another embodiment of the present invention represented by Formula VI, $R^3$ is $C_1$–$C_5$ alkyl substituted by one or more halo.

In a further embodiment of the present invention represented by Formula VI, $R^3$ is $C_1$–$C_5$ alkyl substituted by one or more fluorine.

In still another embodiment of the present invention represented by Formula VI, $R^3$ is methyl substituted by one or more halo.

In yet another embodiment of the present invention represented by Formula VI, $R^3$ is methyl substituted by one or more fluorine. In another embodiment of the present invention represented by Formula VI, $R^3$ is $CH_2F$.

In still another embodiment of the present invention represented by Formula VI, $R^3$ is $C_1$–$C_5$ alkyl substituted by alkoxy.

In a further embodiment of the present invention represented by Formula VI, $R^3$ is methoxy methyl.

In yet another embodiment of the present invention represented by Formula VI, $R^3$ is $C_1$–$C_5$ alkyl.

In another embodiment of the present invention represented by Formula VI, $R^3$ is methyl.

The present invention also includes pharmaceutical compositions that comprise a compound of Formula I, II, III, IV, V, or VI.

Methods of using the compounds of Formula I, II, III, IV, V, or VI include the use of inhibiting nitric oxide synthesis in a subject in need of such inhibition by administering a therapeutically effective amount of the present compound, selectively inhibiting nitric oxide synthesis produced by inducible nitric oxide synthase over nitric oxide produced by the constitutive forms of nitric oxide synthase in a subject in need of such inhibition by administering a therapeutically effective amount of a compound of Formula I, II, III, IV, V, or VI, lowering nitric oxide levels in a subject in need of such by administering a therapeutically effective amount of a compound of Formula I, II, III, IV, V, or VI, lowering nitric oxide levels in a subject in need of such by administering a therapeutically effective amount of a pharmaceutical composition comprising a compound of Formula I, II, III, IV, V, or VI.

The compounds of the present invention may also be used advantageously in combination with a second pharmaceutically active substance, particularly in combination with a selective inhibitor of the inducible isoform of cyclooxygenase (COX-2). Thus, in a further aspect of the invention there is provided the use of a present compound or a pharmaceutically acceptable salt thereof, in combination with a COX-2 inhibitor for the treatment of inflammation, inflammatory disease and inflammatory related disorders. And there is also provided a method of treating, or reducing the risk of, inflammation, inflammatory disease and inflammatory related disorders in a person suffering from or at risk of, said disease or condition, wherein the method comprises administering to the person a therapeutically effective amount of a present compound or a pharmaceutically acceptable salt, thereof in combination with a COX-2 inhibitor. COX-2 inhibitors are illustrated but not limited by Celecoxib Vioxx. The NOS inhibitor and the COX-2 inhibitor may either be formulated together within the same pharmaceutical composition for administration in a single dosage unit, or each component may be individually formulated such that separate dosages may be administered either simultaneously or sequentially.

The term "alkyl", alone or in combination, means an acyclic alkyl radical, linear or branched, containing from 1 to 5, or from 1 to 3 carbon atoms. Said alkyl radicals may be optionally substituted with one or more halo.

The terms "alkoxy" embraces linear or branched oxy-containing radicals each having alkyl portions of one to five carbon atoms, such as methoxy radical. Examples of such radicals include methoxy, ethoxy, propoxy, butoxy and tert-butoxy alkyls.

The term "halo" means halogens such as fluorine, chlorine, bromine or iodine atoms.

Also included in the family of compounds of Formula I, II, III, IV, V, or VI are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula I, II, III, IV, V, or VI may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula I, II, III, IV, V, or VI include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compound of Formula I, II, III, IV, V, or VI by reacting, for example, the appropriate acid or base with the compound of Formula I, II, III, IV, V, or VI.

Although nitrogen protecting groups are illustratively shown as, t-butoxycarbonyl, or t-BOC, any suitable nitrogen protecting group could be substituted in the synthesis of the compounds of the present invention. Numerous protected amino groups useful in the present invention for are described by Theodora W. Greene and Peter G. M. Wuts (*Protective Groups in Organic Synthesis*, 3rd ed., John Wiley & Sons, New York, 1999, pp. 494–653). For example NZ can be a 4-chlorobenzylimino group. In one embodiment of the present invention, the protected amino group is any such group resulting from the reaction of an aldehyde with the corresponding amino group to form a Schiff base. A large variety of deprotecting reagents can be advantageously used in the present invention to effect the conversion of the intermediate to the desired compound. Many such deprotecting reagents are described by Greene and Wuts, supra. For example, when the protected amino group is a 4-chlorobenzylimino group or a t-butoxycarbonylamino group, preferably the deprotecting reagent is an acid. Some useful acid deprotecting agents include, without limitation, hydrochloric acid, hydrobromic acid, sulfuric acid, trifluoroacetic acid, phosphoric acid, phosphorus acid, and acetic acid.

When a compound is described by both a structure and a name, the name is intended to correspond to the indicated structure, and similarly the structure is intended to correspond with the indicated name.

While it may be possible for the compounds of Formula I, II, III, IV, V, or VI to be administered as the raw chemical, it is preferable to present them as a pharmaceutical composition. According to a further aspect, the present invention provides a pharmaceutical composition comprising a compound of Formula I, II, III, IV, V, or VI or a pharmaceutically acceptable salt or solvate thereof, together with one or more pharmaceutically acceptable carriers thereof and optionally one or more other therapeutic ingredients. The carrier(s) must be acceptable in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of Formula I, II, III, IV, V, or VI or a pharmaceutically acceptable salt or solvate thereof with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 0.5 mg to 200 mg, usually around 0.5 mg to 100 mg.

The compounds of Formula I, II, III, IV, V, or VI are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

Compounds of the present invention can exist in tautomeric, geometric or stereoisomeric forms. The present invention contemplates all such compounds, including cis- and trans-geometric isomers and mixtures thereof, E- and Z-geometric isomers and mixtures thereof, R- and S-enantiomers, diastereomers, d-isomers, l-isomers, the racemic mixtures thereof and other mixtures thereof, as falling within the scope of the invention. Pharmaceutically acceptable salts of such tautomeric, geometric or stereoisomeric forms are also included within the invention.

The terms "cis" and "trans" denote a form of geometric isomerism in which two carbon atoms connected by a double bond will each have two highest ranking groups on the same side of the double bond ("cis" or "Z") or on opposite sides of the double bond ("trans" or "E"). Some of the compounds described contain alkenyl groups, and are meant to include both cis and trans or "E" and "Z" geometric forms. Other compounds of the invention include mixtures of both the cis/Z and the trans/E isomers.

The compounds described contain a stereocenter and are meant to include R, S, and mixtures of R and S forms. Some of the compounds described contain geometric isomers and are meant to include E, Z and mixtures of E and Z forms for each stereocenter present.

The following schemes are useful in making the present invention. Where isomers are not defined, utilization of appropriate chromatography methods will afford single isomers.

Scheme 1

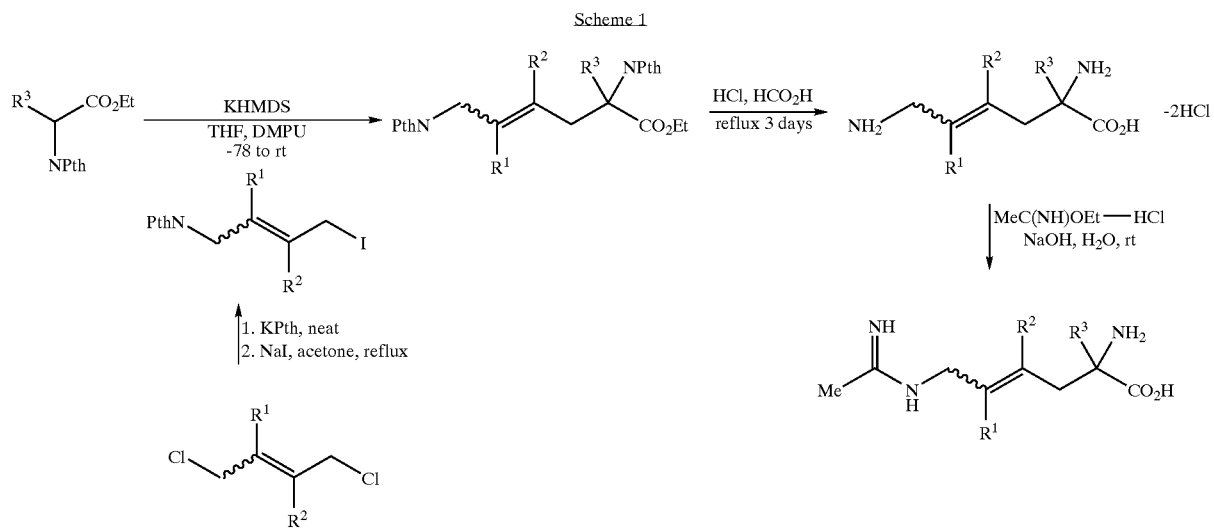

Scheme 2

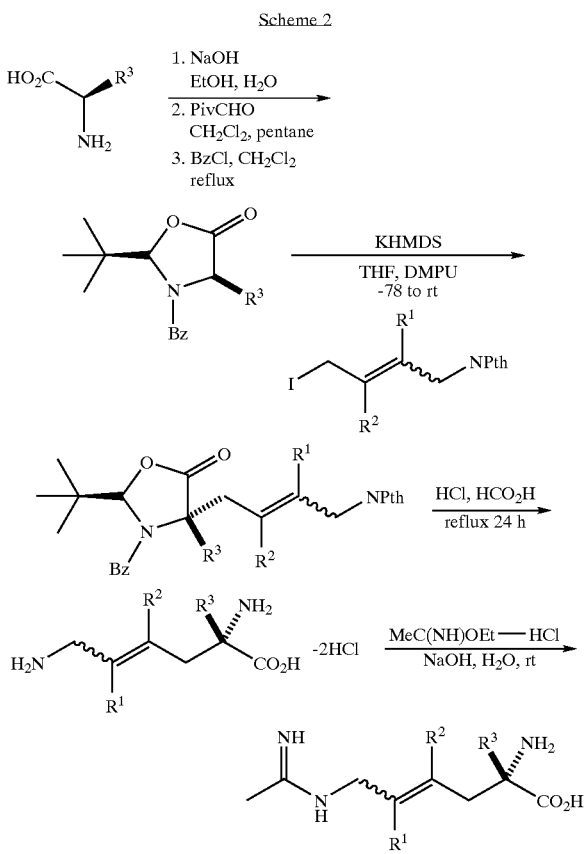

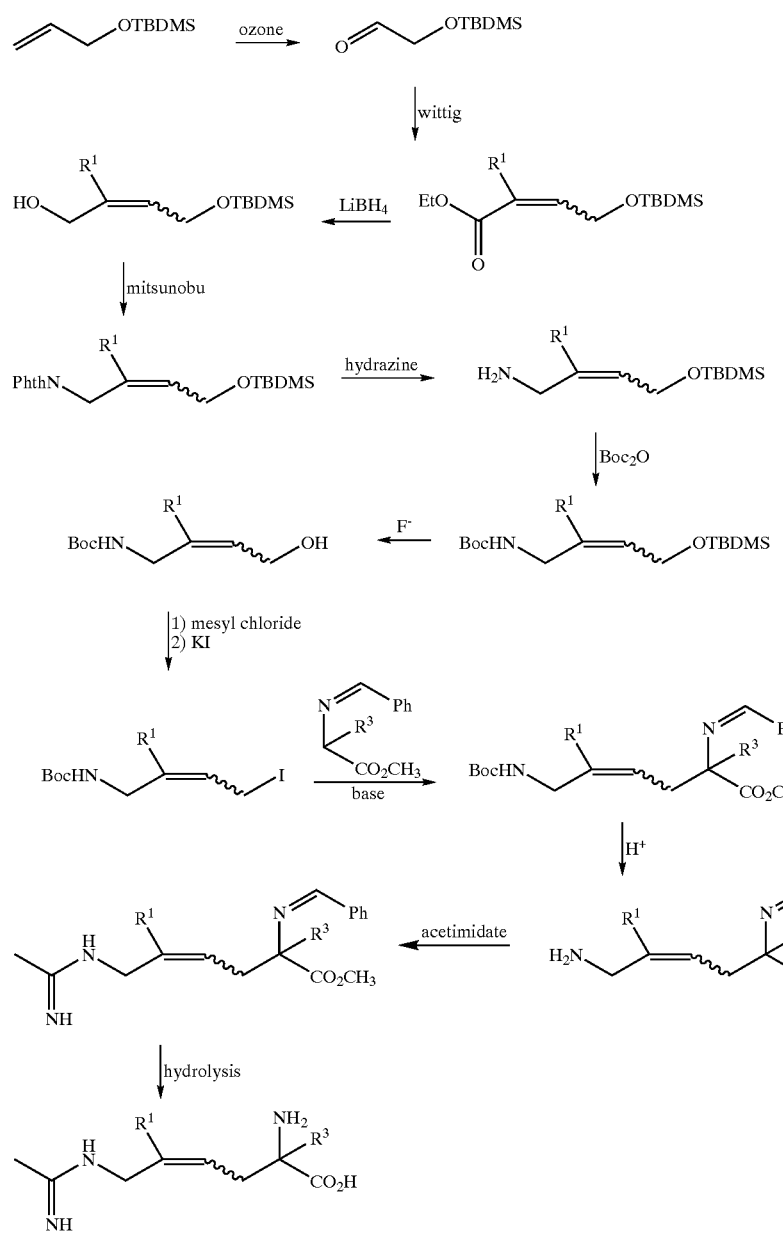
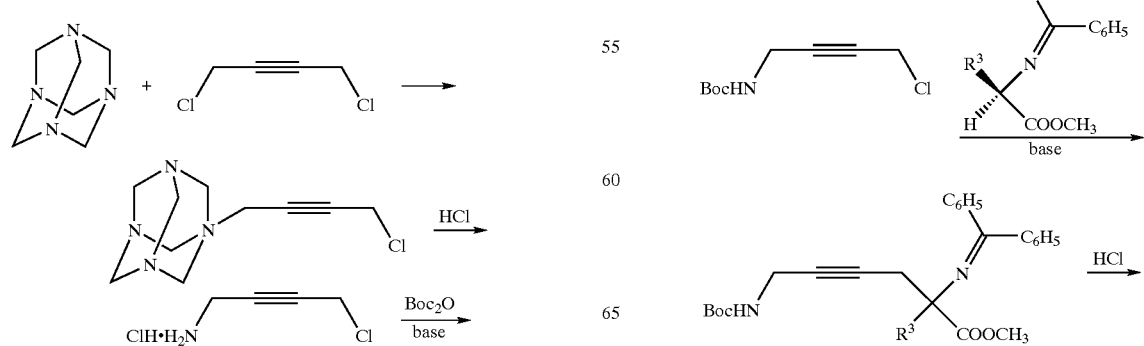

US 6,756,406 B2
25
-continued
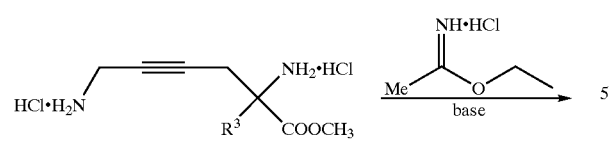
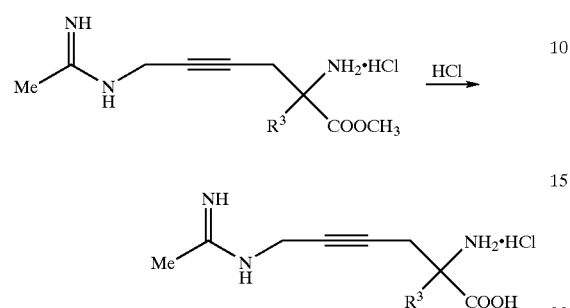
Scheme 5
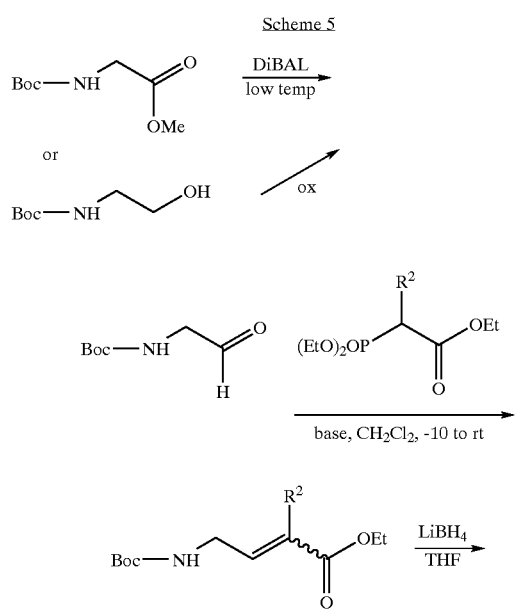
26
-continued
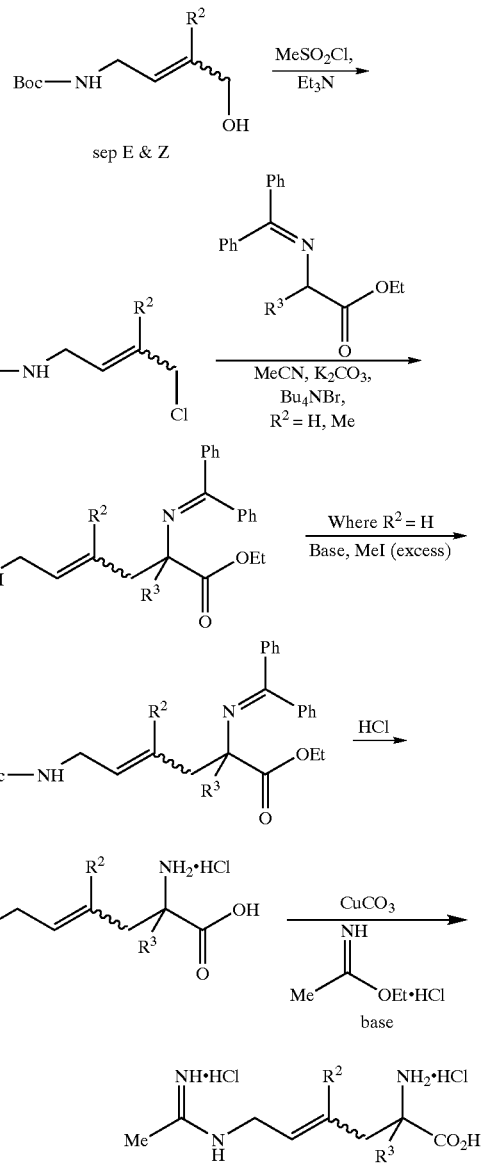
Scheme 6
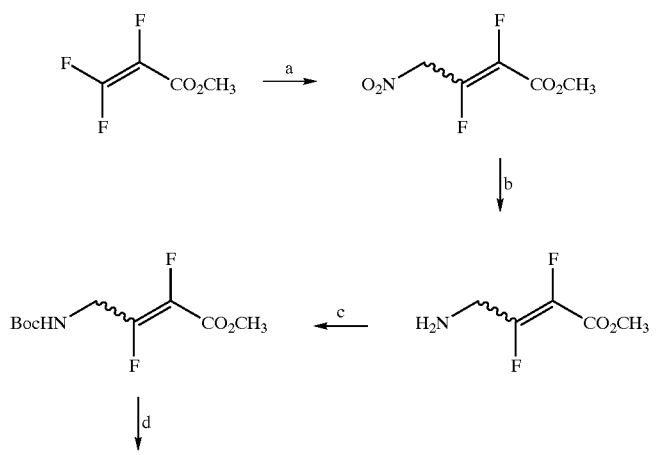

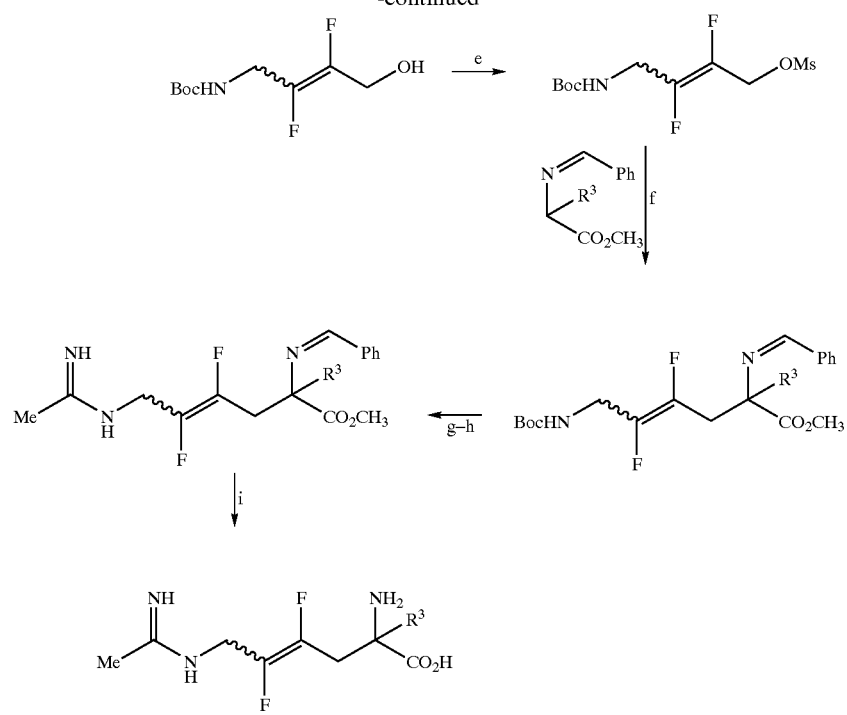
a) nitromethane/base; b) Zn/acetic acid; c) Boc₂O, base; d) DIBAL, low temperature; e) MsCl, base; f) base; g) acid; h) ethyl acetimidate, base; i) acid hydrolysis.
Scheme 7
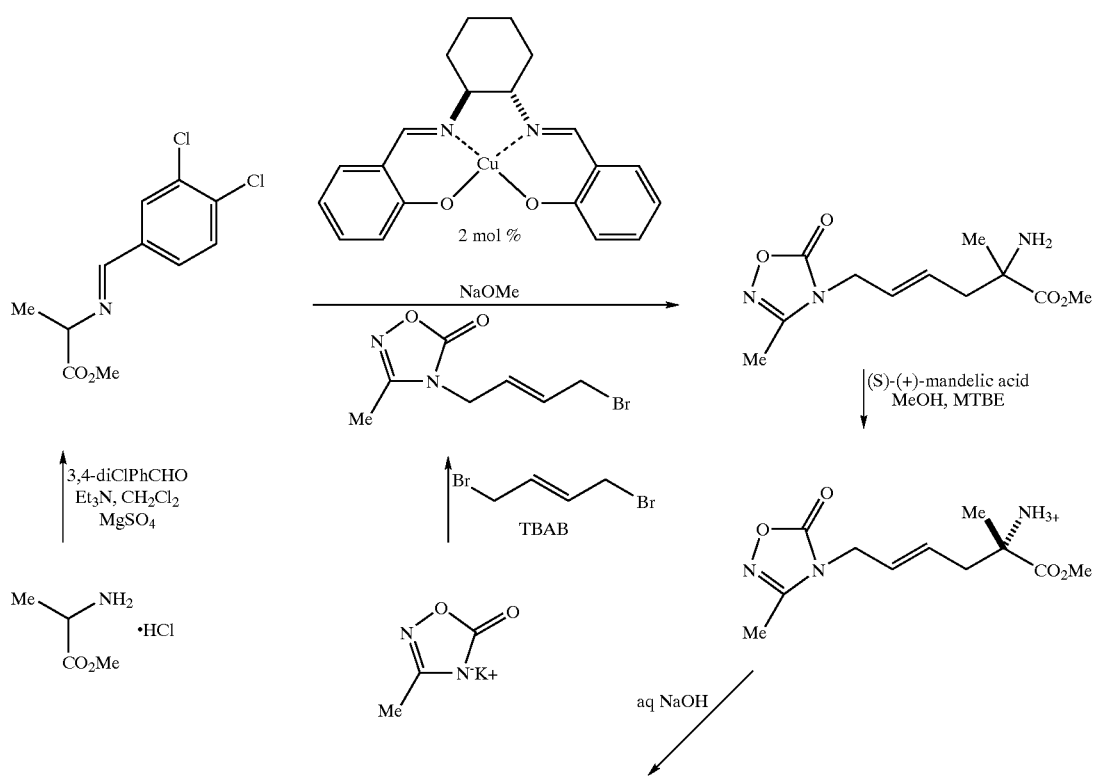

-continued

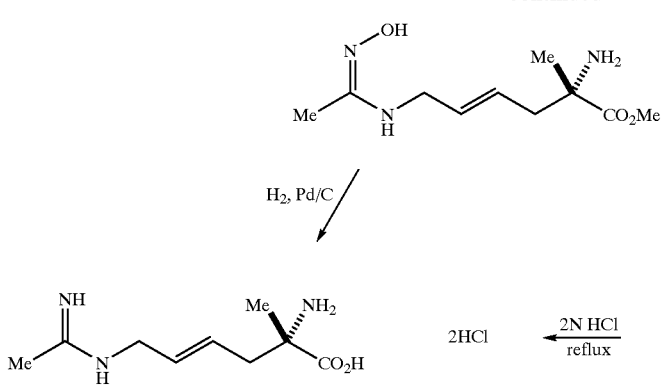

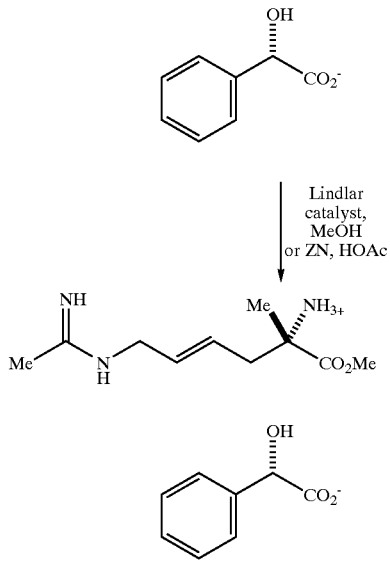

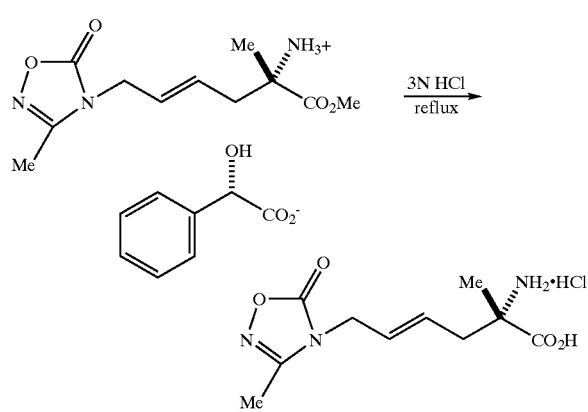

The following Examples are illustrative and not intended to limit the scope of the invention.

EXAMPLE 1

(E)-2-amino-2-methyl-6-[(1-iminoethyl)amino]-4-hexenoic acid, dihydrochloride

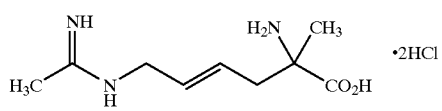

EXAMPLE 1a

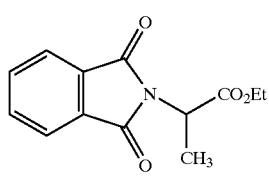

DL-Alanine ethyl ester hydrochloride (5 g, 32.5 mmol) was suspended in toluene (50 mL). Triethyl amine (4.5 mL, 32.5 mmol) was added followed by phthalic anhydride (4.8 g, 32.5 mL). The reaction flask was outfitted with a Dean-Stark trap and reflux condenser and the mixture was heated at reflux overnight.

Approximately 10 mL of toluene/water was collected. The reaction mixture was cooled to room temperature and diluted with aqueous $NH_4Cl$ and EtOAc. The layers were separated and the aqueous layer was extracted with EtOAc (3×). The ethyl acetate extract was washed with brine, dried over $MgSO_4$, filtered and concentrated in vacuo to give the title phthalyl-protected amino ester as a white crystalline solid in near quantitative yield.

$^1$H NMR (400 MHz, $CDCl_3$, δ ppm): 1.2 (t, 3H), 1.6 (d, 3H), 4.2 (m, 2H), 4.9 (q, 1H), 7.7 (m, 2H), 7.9 (m, 2H)

EXAMPLE 1b

Potassium phthalimide (18.5 g, 0.1 mol) was added to a 250 mL round bottomed flask containing 1,4-butene dichloride (25 g, 0.2 mol). The reaction mixture was heated to 150° C. for 1.5 h. The mixture was cooled to room temperature and was partitioned between brine and $Et_2O$. The organic layer was dried with $MgSO_4$, filtered and concentrated in vacuo. The residue was recrystallized from hot ethanol to give the title 1-chloro-4-phthalimidobutene (8.9 g, 39%) as orange crystals.

HRMS calcd. For $C_{12}H_{10}ClNO_2$: m/z=236.0478 [M+H]. Found: 236.0449 $^1$H NMR (300 MHz, $CDCl_3$, δ ppm): 4.1 (d, 2H), 4.3 (d, 2H), 5.9 (m, 2H), 7.7 (m, 2H), 7.9 (m, 2H)

EXAMPLE 1c

A sample of the product of Example 1b (2.3 g, 9.8 mmol) was dissolved in acetone (50 mL). NaI (3.2 g, 21 mmol) was added and the mixture was refluxed overnight. After cooling to room temperature, $Et_2O$ was added and the mixture was washed sequentially with sodium thiosulfate and brine. The organic layer was dried with $MgSO_4$, filtered and concentrated in vacuo to give the title iodide (2.8 g, 87.5%) as a light yellow solid that was used without further purification.

$^1$H NMR (400 MHz, $CDCl_3$, δ ppm): 3.8 (d, 2H), 4.2 (d, 2H), 5.7 (m, 1H), 6.0 (m, 1H), 7.7 (m, 2H), 7.9 (m, 2H) Mass (M+1)=328

EXAMPLE 1d

A solution of KHMDS (2.6 g, 13.3 mmol) in THF (50 mL) was cooled to −78° C. A solution of the product of Example 1a (2.2 g, 8.87 mmol) in THF (15 mL) was added and 1,3-dimethyl-3,4,5,6-tetrahydro-2(1H)-pyrimidinone (DMPU, 1.0 mL, 8.87 mL) was added immediately thereafter. After the solution was stirred at −78° C. for 40 minutes, a solution of the product of Example 1c (2.9 g, 8 87 mmol) in THF (15 mL) was added. The flask was removed from the cold bath and was stirred at room temperature for 3 h. The reaction mixture was partitioned between saturated aqueous $NaHCO_3$ and EtOAc. The organic extract was washed with brine, dried over $MgSO_4$, filtered and concentrated in vacuo to give the desired bis-pththalyl protected amino ester as a yellow solid. This residue was chromatographed on silica gel (1:1 hexanes: EtOAc) and gave 1.4 g (35%) of the title material as a white solid.

$^1$H NMR (300 MHz, $CDCl_3$, δ ppm): 1.2 (t, 3H), 1.6 (d, 3H), 2.8 (dd, 1H), 3.1 (dd, 1H), 4.2 (m, 4H), 5.6 (m, 11H), 5.8 (m, 1IH), 7.6 (m, 4H), 7.7 (m, 2H), 7.9 (m, 2H) Mass (M+H)=447

EXAMPLE 1e

The product of Example 1d (0.78 g, 1.76 mmol) was dissolved in a mixture of formic acid (10 mL, 95%) and HCl (20 mL, concentrated HCl) and was refluxed for 3 days. The reaction mixture was cooled to 0° C. and filtered to remove phthalic anhydride. After concentrating in vacuo (T<40° C.), the title unsaturated alpha methyl lysine was obtained as a white solid (0.38 g, 95%), which was used without further purification.

$^1$H NMR (300 MHz, $D_2O$, δ ppm): 1.4 (s, 3H), 2.4 (dd, 1H), 2.6 (dd, 1H), 3.5 (d, 2H), 5.7 (m, 2H) Mass(M+H)=317

EXAMPLE 1

The product of Example 1e (0.2 g, 0.86 mmol) was dissolved in $H_2O$ (8 mL) and was brought to pH 9 with 2.5 N NaOH. Ethyl acetimidate—HCl (0.42 g, 3.4 mmol) was added in four portions over 1 h. After 1 h, the mixture was acidified to pH 4 with 10% HCl and was concentrated in vacuo. The residue was then passed through a water-washed DOWEX 50WX4-200 column (H form, 0.5 N $NH_4OH$ eluent). The residue was concentrated in vacuo, acidified to pH 4 with 10% HCl, and concentrated to give the title product (17 mg, 6%) as an oil.

HRMS calcd. For $C_9H_{17}N_3O_2$: m/z=200.1399 [M+H]. Found: 200.1417 $^1$H NMR (400 MHz, $D_2O$, δ ppm): 1.4 (s, 3H), 2.1 (s, 3H), 2.5 (dd, 1H), 2.6 (dd, 1H), 3.8 (d, 2H), 5.6 (m, 2H)

EXAMPLE 2

(S,E)-2-amino-2-methyl-5-fluoro-6-[(1-iminoethyl)amino]-4-hexenoic acid, dihydrochloride

EXAMPLE 3

(S,E)-2-amino-2-methyl-4-fluoro-6-[(1-iminoethyl)amino]-4-hexenoic acid, dihydrochloride

EXAMPLE 4

(S,E)-2-amino-2-methyl-4,5-difluoro-6-[(1-iminoethyl)amino]-4-hexenoic acid, dihydrochloride

EXAMPLE 5

(R,E)-2-amino-2-methyl-6-[(1-iminoethyl)amino]-4-hexenoic acid, dihydrochloride

EXAMPLE 5a

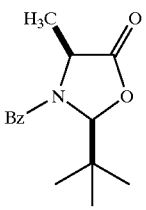

(2S, 4S)-3-Benzoyl-2-(tert-butyl)-4-methyl-1,3-oxazolidin-5-one was prepared according to Seebach's procedure. Seebach, D.; Fadel, A. Helvetica Chimnica Acta 1985, 68, 1243.

EXAMPLE 5b

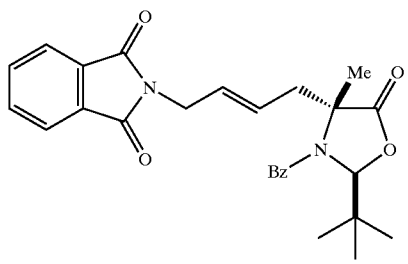

A solution of KHMDS (0.65 g, 3.24 mmol), DMPU (0.33 mL, 2.7 mmol) and THF (40 mL) was cooled to −78° C. A solution of (2S, 4S)-3-benzoyl-2-(tert-butyl)-4-methyl-1,3-oxazolidin-5-one 5a (0.70 g, 2.7 mmol) in THF (10 mL) was added dropwise. After 45 min, a solution of the product of Example 1c (0.88 g, 2.7 mmol) in THF (10 mL) was added. The reaction mixture was stirred at room temperature for 2 h and quenched with saturated aqueous $NaHCO_3$. The layers were separated and the aqueous layer was extracted with EtOAc. The organic layers were combined and washed with brine, dried over $MgSO_4$, filtered and concentrated in vacuo. The resulting yellow oil was chromatographed on silica gel (9:1 then 4:1 hexanes/ethyl acetate) to give the title protected unsaturated alpha methyl D-lysine (0.26 g, 20%) as a colorless oil.

HRMS calcd. For $C_{27}H_{28}N_2O_5$: m/z=461.2076[M+H]. Found: 461.2033 $^1$H NMR (400 MHz, $CDCl_3$, δ ppm): 0.9 (s, 9H), 1.5 (s, 3H), 4.3 (m, 2H), 5.5 (m, 2H), 5.6 (m, 2H), 6.1 (m, 1H), 7.5 (m, 5H), 7.7 (m, 2H), 7.9 (m, 2H)

EXAMPLE 5c

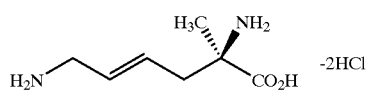

The product of Example 5b (0.255 mg, 0.55 mmol) was dissolved in 6N HCl (6 mL) and formic acid (6 mL) and was heated to reflux for 24 h. The reaction mixture was cooled to room temperature and concentrated in vacuo. The residue was suspended in water and washed with $CH_2Cl_2$. The aqueous layer was concentrated and passed through a water-washed DOWEX 50WX4-200 column (H form, 0.5 N $NH_4OH$ eluent). The residue was concentrated in vacuo, acidified to pH 4 with 10% HCl, and concentrated to give the title unsaturated D-lysine (71 mg, 55%) as an oil which was used without further purification.

$^1$H NMR (400 MHz, $D_2O$, δ ppm): 1.4 (s, 3H), 2.5 (dd, 1H), 2.6 (dd, 1H), 3.4 (d, 2H), 5.6 (m, 2H), 5.7 (m, 2H)

EXAMPLE 5

The product of Example 5c (13 mg, 0.056 mmol) was dissolved in $H_2O$ (5 mL) and was brought to pH 9 with 2.5 N NaOH. Ethyl acetimidate—HCl (27 mg, 0.2 mmol) was added in four portions over 2 h. After 2 h, the mixture was acidified to pH 4 with 10% HCl and was concentrated in vacuo. The residue was passed through a water-washed DOWEX 50WX4-200 column (H form, 0.5 N $NH_4OH$ eluent). The residue was concentrated in vacuo, acidified to pH 4 with 10% HCl, and concentrated to give the title product (45 mg) as an oil.

HRMS calcd. For $C_9H_{17}N_3O_2$: m/z=200.1399 [M+H]. Found: 200.1386 $^1$H NMR (400 MHz, $D_2O$, δ ppm): 1.4 (s, 3H), 2.1 (s, 3H), 2.5 (dd, 1H), 2.6 (dd, 1H), 3.8 (d, 2H), 5.6 (m, 2H)

EXAMPLE 6

(S,E)-2-amino-2-methyl-6-[(1-iminoethyl)amino]-4-hexenoic acid, dihydrochloride

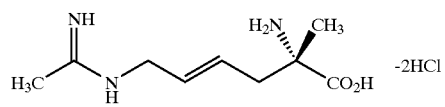

EXAMPLE 6a

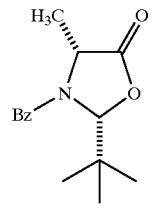

(2R,4R)-3-Benzoyl-2-(tert-butyl)-4-methyl-1,3-oxazolidin-5-one was prepared according to Seebach's procedure. Seebach, D.; Fadel, A. Helvetica Chimica Acta 1985, 68, 1243.

EXAMPLE 6b

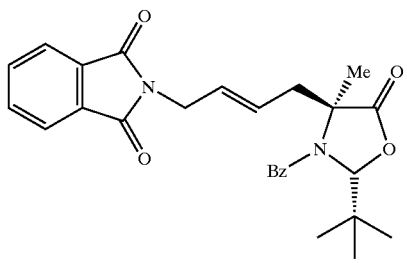

A solution of the (2R,4R)-3-benzoyl-2-(tert-butyl)-4-methyl-1,3-oxazolidin-5-one product of Example 6a (2.0 g, 7.6 mmol) in THF (50 mL) was cooled to −78° C. A −78° C. solution of KHMDS (0.65 g, 3.24 mmol) in THF (25 mL) was added dropwise. After 30 min, a solution of the product of Example 1c (2.8 g, 8.6 mmol) in THF (25 mL) was added. The reaction mixture was stirred at room temperature for 1 h and quenched with saturated aqueous NaHCO$_3$. The layers were separated and the aqueous layer was extracted with EtOAc. The organic layers were combined and washed with brine, dried with MgSO$_4$, filtered and concentrated in vacuo. The resulting orange oil was chromatographed on silica gel (9:1 then 4:1 hexanes/ethyl acetate) to give the protected title unsaturated alpha methyl L-lysine (0.5 g, 15%) as a white solid.

HRMS calcd. For C$_{27}$H$_{28}$N$_2$O$_5$: m/z=461.2076[M+H]. Found: 461.2043 $^1$H NMR (400 MHz, CDCl$_3$, δ ppm): 0.9 (s, 9H), 1.5 (s, 3H), 4.3 (m, 2H), 5.5 (m, 2H), 5.6 (m, 2H), 6.1 (m, 1H), 7.5 (m, 5H), 7.7 (m, 2H), 7.9 (m, 2H)

EXAMPLE 6c

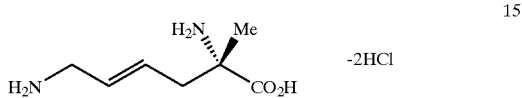

The product of Example 6b (0.5 g, 1 mmol) was dissolved in 12N HCl (10 mL) and formic acid (5 mL) and this mixture was heated to reflux for 12 h. The reaction mixture was cooled in the freezer for 3 h and the solids were removed by filtration. The residue was washed with CH$_2$Cl$_2$ and EtOAc. The aqueous layer was concentrated in vacuo and gave the title unsaturated alpha methyl L-lysine (0.26 g, 99%) as an oil which was used without further purification.

$^1$H NMR (300 MHz, D$_2$O, δ ppm): 1.4 (s, 3H), 2.5 (dd, 1H), 2.6 (dd, 1H), 3.4 (d, 2H), 5.7 (m, 2H)

EXAMPLE 6

The product of Example 6c (0.13 g, 0.56 mmol) was dissolved in H$_2$O (1 mL) and was brought to pH 9 with 2.5 N NaOH. Ethyl acetimidate—HCl (0.28 g, 2.2 mmol) was added in four portions over 1 h. After 1 h, the mixture was acidified to pH 4 with 10% HCl and was concentrated in vacuo. The residue was and passed through a water-washed DOWEX 50WX4-200 column (0.5 N NH$_4$OH eluent). The residue was concentrated in vacuo, acidified to pH 4 with 10% HCl, and concentrated to give the title product as an oil (40 mg).

HRMS calcd. For C$_9$H$_{17}$N$_3$O$_2$: m/z=222.1218 [M+Na]. Found: 222.1213 $^1$H NMR (300 MHz, D$_2$O, δ ppm): 1.4 (s, 3H), 2.1 (s, 3H), 2.4 (dd, 1H), 2.6 (dd, 1H), 3.8 (d, 2H), 5.6 (m, 2H)

EXAMPLE 7
2-amino-2-methyl-6-[(1-iminoethyl)amino]-4-hexynoic acid, dihydrochloride

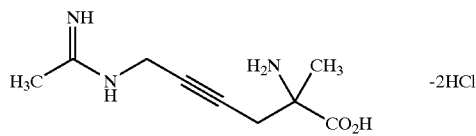

EXAMPLE 7a

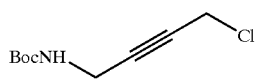

The N-boc-1-amino-4-chlorobut-2-yne was prepared following the procedure described in Tetrahedron Lett. 21, 4263 (1980).

EXAMPLE 7b

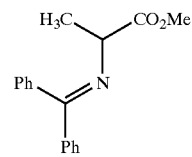

Methyl N-(diphenylmethylene)-L-alaninate was prepared by following the procedure described in J. Org. Chem., 47, 2663 (1982).

EXAMPLE 7c

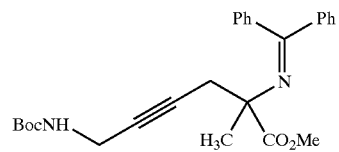

Dry THF (1000 mL) was placed in a flask purged with argon and 60% NaH dispersed in mineral oil (9.04 g, 0.227 mol) was added. To this mixture was added the product of Example 7b (30.7 g, 0.114 mol). The reaction mixture was then stirred at 10° C.–15° C. for 30 min. Potassium iodide (4 g) and iodine (2 g) were added and immediately followed by the addition of the product of Example 7a (23 g, 0.113 mol in 200 mL THF) in 30 min. The reaction mixture was then stirred at 55° C. until the starting material disappeared (~2 h). The reaction mixture was then cooled to room temperature and the solvent was evaporated. Ethyl acetate (500 mL) was added and the mixture was carefully washed with 2×200 mL deionized water. The organic layer was dried over anhydrous MgSO$_4$, filtered and evaporated to give 44 g of crude product. Purification by chromatography using 20% ethyl acetate in hexane afforded the title protected unsaturated alpha-methyl lysine (28 g, 57%).

Anal.Calcd for C$_{26}$H$_{30}$N$_2$O$_4$ and 0.5 ethylacetate: C, 70.42; H, 7.14; N, 5.91. Found: C, 70.95; H, 7.73; N, 6.09 IR (Neat, λ max, cm$^{-1}$): 2981, 1714, 1631 $^1$H NMR (CDCl$_3$, δ ppm): 1.28 (s, 9H), 1.4 (s, 3H), 2.65–2.76(m, 2H), 3.15 (s, 3H), 3.7 (bs, 2H), 4.6 (bs, 1H), 6.95–7.4 (m, 10H) $^{13}$C NMR (CDCl$_3$, δ ppm): 24.29, 28.33, 28.39, 33.24, 51.60, 53.55, 127.79, 127.97, 128.26, 128.36, 128.43, 128.54, 128.66, 130.05, 130.22, 132.39 Mass (M+1)=435 DSC purity: 261.95° C.

EXAMPLE 7d

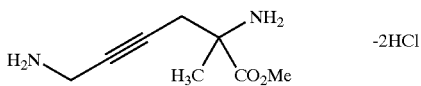

The product of Example 7c (16 g, 0.0368 mol) was dissolved in 1N HCl (300 mL) and stirred at 25° C. for 2 h. The reaction mixture was washed with ether (2×150 mL) and the aqueous layer separated and decolorized with charcoal. Concentration afforded ~9 g (100% yield) of the deprotected unsaturated alpha-methyl lysine ester 7d as white foamy solid.

Anal.Calcd for $C_8H_{14}N_2O_2$ containing 2.26 HCl and 1.19 $H_2O$: C,35.06; H, 6.86; N, 10.22; Cl, 29.24. Found: C, 35.31; H, 7.38; N, 10.70; Cl, 29.77. $^1$H NMR ($D_2O$, δ ppm): 1.56 (s, 3H), 2.8–3.0 (2 dt, 2H), 3.75 (s, 2H), 3.79 (s, 3H) $^{13}$C NMR ($D_2O$, δ ppm): 23.89, 29.81, 32.05, 57.08, 61.90, 79.57, 82.43, 173.92 Mass (M+1)=171 DSC purity: 114.22° C. UV=206 nm,abs 0.013 $[a]_{25}$ in methanol=0 at 365 nm

EXAMPLE 7e

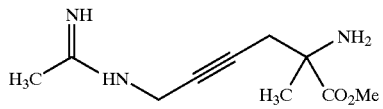

The product of Example 7d (2.43 g, 0.01 mol) was dissolved in deionized water (25 mL). A solution of NaOH (400 mg, 0.01 mol) in deionized water (25 mL) was added at 25° C. to bring the pH to ~7.95 and stirring was continued another 10 min. Ethylacetimidate hydrochloride (988 mg, 0.008 mol) was added to the reaction mixture with simultaneous adjustment of the pH to ~8.5 by adding 1N NaOH. The reaction mixture was stirred at pH 8 to 8.5 for 3 h following acetimidate addition. 1N HCl was added to the reaction mixture (4.1 pH). The solvent was evaporated at 50° C. to afford a yellow crude hygroscopic residue (4 g, >100% yield). Purification was carried out on the Gilson chromatography system using 0.1% $AcOH/CH_3CN/H_2O$.

Anal.Calcd for $C_{10}H_{17}N_3O_2$ containing 2.25 HCl and 1.7 $H_2O$: C, 37.08; H, 7.05; N, 12.97; Cl, 24.63. Found: C, 37.01; H, 6.79; N, 12.76; Cl, 24.87 IR (Neat, λ max, $cm^{-1}$): 2953, 2569, 1747, 1681, 1631 $^1$H NMR ($D_2O$, δ ppm): 1.52 (s, 3H), 2.12 (s, 3H), 2.74–2.96 (2 dt, 2H), 3.75 (s, 3H), 3.95 (t, 2H) $^{13}$C NMR ($D_2O$, δ ppm): 23.89, 29.81, 32.05, 57.08, 61.90, 79.57, 82.43, 173.92 Mass (M+1)=212

EXAMPLE 7

The product of Example 7e (100 mg, 0.0005 mol) was dissolved in 8N HCl (20 mL) and stirred for 10 h at reflux. The reaction mixture was cooled to room temperature and the aq. HCl was evaporated on rotavap. The residue was dissolved in deionized water (10 mL) and water and reconcentrated under vacuum to afford the title product as a yellow glassy solid in almost quantitative yield (88 mg).

Anal.Calcd for $C_9H_{15}N_3O_2$ containing 2.4 HCl and 1.8 $H_2O$: C, 34.08; H, 6.67; N, 13.25; Cl, 26.83. Found: C, 34.32; H, 6.75; N, 13.63; Cl, 26.47 IR (Neat, λ max, $cm^{-1}$): 1738, 1677, 1628, 1587 $^1$H NMR ($D_2O$, δ ppm): 1.6 (s, 3H), 2.24 (s, 3H), 2.8–3.0 (2 dt, 2H), 4.1 (s, 2H) $^{13}$C NMR ($D_2O$, δ ppm): 21.22, 24.10, 29.88, 34.58, 80.04, 80.99, 128.39, 168.07, 176.13 Mass (M+1)=198

EXAMPLE 8
(Z)-2-amino-2-methyl-6-[(1-iminoethyl)amino]-4-hexenoic acid, dihydrochloride

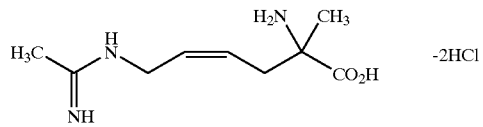

EXAMPLE 9
(S,E)-2-amino-2-methyl-6-[(1-iminoethyl)amino]-4-hexenoic acid, dihydrochloride

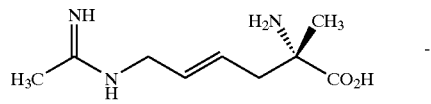

EXAMPLE 9a

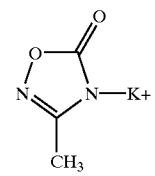

The potassium salt of 3-methyl-1,2,4-oxadiazol-5(4H)-one was prepared as previously described by Moussebois, C., Eloy, F. Helv. Chim. Acta, 47(3), 838–48, (1964).

EXAMPLE 9b

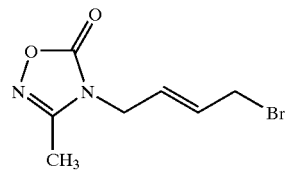

A 1 L flask was charged with trans-1,4-dibromo-2-butene (50 g, 0.23 mol) and acetone (500 mL). The heterocycle product of Example 9a (16 g, 0.12 mol) was added, followed by tetra-n-butyl ammonium bromide (3.9 g, 0.012 mol, 0.1 equiv). The reaction mixture was stirred at rt for 18 h, diluted with brine and extracted with EtOAc. The organic extract was washed with brine, dried over $MgSO_4$, filtered and concentrated in vacuo to give a yellow semi-solid residue. Methylene chloride was added and solid product was removed by filtration. The filtrate was concentrated and the residue was treated with hot hexanes to dissolve the unreacted dibromobutene. The hexanes layer was decanted and the resulting oil was chromatographed on silica, eluting with 7:3 hexanes/EtOAc. The title product (14.2 g, 50%) was isolated in the form of a yellow oil.

$^1$H NMR (300 MHz, $CDCl_3$, δ ppm) 2.2 (s, 3H), 3.9 (d, 2H), 4.2 (d, 2H), 5.7 (dt, 1H), 5.9 (dt, 1H)

EXAMPLE 9c

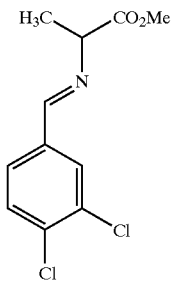

To a slurry of D,L-alanine methyl ester hydrochloride (16.83 g, 120.5 mmol) in CH$_2$Cl$_2$ (400 mL) was added triethylamine (16.2 mL, 116.4 mmol) followed by 3,4-dichlorobenzaldehyde (19.07 g, 109 mmol) and MgSO$_4$ (20 g). The slurry was stirred at room temperature for 18 hours and filtered. The filtrate was washed with water (250 mL) and brine (250 mL), dried (MgSO$_4$) and evaporated to give 27.65 g (97%) of the desired imine as an oil.

$^1$H NMR (300 MHz, C$_6$D$_6$, δ ppm): 1.40 (d, 3H), 3.32 (s, 3H), 3.81 (q, 1H), 6.82 (d, 1H), 7.18 (dd, 1H), 7.53 (d, 1H), 7.58 (s, 1H)

EXAMPLE 9d

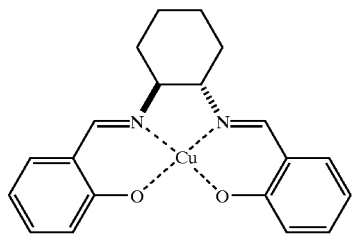

The (1S,2S)-(+) Cu(II)C$_6$Salen chiral phase transfer catalyst was prepared following the procedure described in Inorganic Chemistry 1996, 35, 387.

EXAMPLE 9e

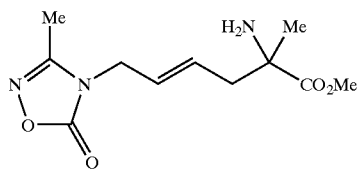

In a N$_2$-flushed, oven dried glassware, sodium methoxide (7.3 g, 134 mmol) was suspended in dry toluene (300 mL). The chiral phase transfer catalyst product of Example 9d (800 mg, 1.9 mmol, 5% based on imine) was added followed by a solution off the product of Example 9c (10 g, 38.5 mmol) in dry toluene (503 mL). A solution of the product of Example 9b (10 g, 42.9 mmol) in 50 mL of toluene was added and the reaction was stirred at room temperature for 18 h. The reaction mixture was then filtered through a pad of Celite to remove NaBr and the catalyst. The toluene layer was treated with 200 mL of 6N HCl for 40 minutes. The layers were separated, the toluene layer was washed with 200 mL of 6N HCl and the combined aqueous layers were concentrated in vacuo. The residue was diluted with 100 mL of water and brought to pH 7 with saturated aqueous K$_2$CO$_3$. The solids were filtered off over a pad of Celite and the filtrate was brought to pH 9. This was extracted with EtOAc (6×), dried with Na$_2$SO$_4$, filtered and concentrated in vacuo to give the title free base as a light green oil (5.77 g, 59%). Chromatography on a chiral column (ChiralPak AD, 70:30 hexanes: iPrOH, 30 min run) gave a product having a ratio of 47:1 (S:R). (S t$_r$=12.2 min, R t$_r$=16.5 min).

$^1$H NMR (300 MHz, CDCl$_3$, δ ppm): 1.4 (s, 3H), 2.2 (s, 3H), 3.7 (s, 3H), 4.2 (d, 2H), 5.6 (m, 2H)

EXAMPLE 9f (2S)-hydroxy(phenyl)ethanoic acid salt of Methyl (2S,4E)-2-amino-2-methyl-6-(3-methyl-5-oxo-1,2,4-oxadiazol-4(5H)-yl)hex-4-enoate

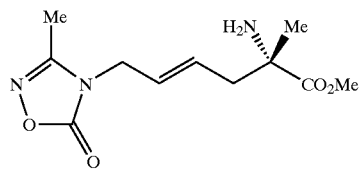

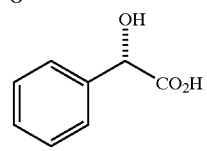

To a solution of the product of Example 9e (2.5 1 g, 9.84 mmol) in MeOH (40 mL) was added (S)-(+)-mandelic acid (1.5 g, 9.84 mmol). The sample was concentrated in vacuo and was then recrystallized from MTBE-MeOH (4:1) to give the title product as a white powder (2.65 g, 66%). Chromatography on a chiral column (ChiralPak AD, 70:30 hexanes: iPrOH, 30 min run) showed a ratio in the title product of 99:1 (S:R). (S t$_r$=12.2 min, R t$_r$=16.5 min).

$^1$H NMR (300 MHz, CD$_3$OD, δ ppm): 1.5 (s, 3H), 2.2 (s, 3H), 2.6 (m, 2H), 3.8 (s, 3H), 4.2 (d, 2H), 5.6 (m, 2H), 7.2 (m, 3H), 7.6 (d, 2H) HRMS calcd. For C$_{10}$H$_{19}$N$_3$O$_2$: m/z= 214.1550 [M+H]. Found: 214.1525

EXAMPLE 9g (2S)-hydroxy(phenyl)ethanoic acid, formic acid salt of Methyl (S,E)-2-amino-2-methyl-6-[(1-iminoethyl)amino]-4-hexenoate

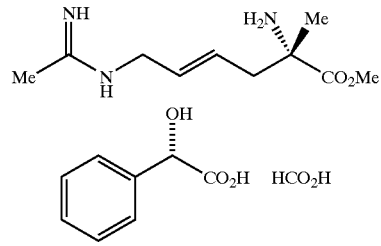

A 500 mL flask was charged with Lindlar catalyst (217 mg, 5 weight %, 5% Pd on CaCO$_3$, poisoned with Pb), MeOH (80 mL), and formic acid (2 mL, 5 equiv.). A slurry of the product of Example 9f (4.34 g, 10.7 mmol) in MeOH (20 mL) was added and the reaction mixture was heated at 60° C. After 4 h, an additional 30 mg of Lindlar catalyst and formic acid (200 μL) were added. The reaction mixture was slurried with Celite, filtered and concentrated in vacuo to give the title material existing as a yellow oil which was used without further purification (97%).

Elemental analyses Calcd for C$_{19}$H$_{29}$N$_3$O$_7$ with 1.3 H$_2$O: C, 52.48; H, 7.32; N, 9.66. Found: C, 52.71; H, 7.01; N, 9.29
$^1$H NMR (300 MHz, D$_2$O, δ ppm): 1.4 (s, 3H), 2.1 (s, 3H), 2.5 (m, 2H), 3.7 (s, 3H), 3.8 (d, 2H), 4.9 (s, 1H), 5.6 (m, 2H), 7.3 (m, 5H), 8.2 (s, 2H) HRMS calcd. For C$_{10}$H$_{19}$N$_3$O$_2$: m/z=214.1550 [M+H]. Found: 214.1544

EXAMPLE 9h

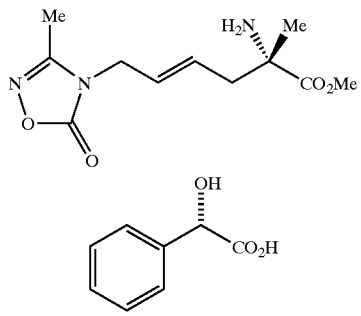

A dry, N$_2$-flushed flask was charged with NaOMe (71.7 g, mmol, 1.3 mol) and dry toluene (2 L). Catalyst product of Example 9d (5.88 g, 15 mmol) was added, followed by a solution of product of Example 9c (10 g, 0.38 mol) in 200 mL of toluene. A solution of the bromide product of Example 9b (10 g, 0.43 mol) in 200 mL of toluene was added dropwise. The reaction was quenched by diluting it with toluene and glacial HOAc while the temperature was maintained at 25° C. After stirring for 15 min at room temperature, the reaction mixture was filtered and the cake was washed with toluene. The filtrate was diluted with H$_2$O and was stirred for 1 h. The layers were separated and the toluene layer was washed with H$_2$O. The aqueous layers were combined and concentrated in vacuo. The residue was dissolved in 120 mL of MeOH and (S)-(+)-mandelic acid was added. Hot methyl tert-butyl ether (450 mL) was added, the solution was cooled to room temperature and stored in the freezer overnight. The title product precipitate was collected and washed with cold methyl tert-butyl ether (43.94 g, 28%). Chromatography on a chiral column (ChiralPak AD, 70:30 hexanes: iPrOH, 30 min run) showed the title product to exist in a ratio of 99:1 (S:R). (S $t_r$=12.2 min, R $t_r$=16.5 min).

$^1$H NMR (300 MHz, CD$_3$OD, δ ppm): 1.5 (s, 3H), 2.2 (s, 3H), 2.6 (m, 2H), 3.8 (s, 3H), 4.2 (d, 2H), 5.6 (m, 2H), 7.2 (m, 3H), 7.6 (d, 2H) HRMS calcd. For C$_{10}$H$_{19}$N$_3$O$_2$: m/z=214.1550 [M+H]. Found: 214.1525

EXAMPLE 9i

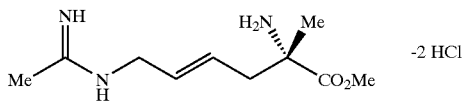

A sample of the product of Example 9h (36.8 g, 90 mmol) was dissolved in water (370 mL), brought to pH 9 with saturated aqueous K$_2$CO$_3$ and extracted with CH$_2$Cl$_2$. The organic extract was concentrated in vacuo to give the free base. This residue was dissolved in a mixture of 1-butanol (184 mL), glacial acetic acid (148 mL) and water (184 mL). Zinc dust (37 g, 0.57 mol) was added as the reaction mixture was stirred vigorously and heated to 50° C. overnight. The solution was filtered through Celite and the filter cake was washed with MeOH. The filtrate was concentrated, dissolved in water (250 mL) and MeOH (55 mL), and the pH brought to 8 with saturated aqueous NaHCO$_3$. The solution was filtered and the filtrate brought to pH 2 with 6N HCl before it was concentrated in vacuo to give the title material.

$^1$H NMR (300 MHz, D$_2$O, δ ppm): 1.4 (s, 3H), 2.1 (s, 3H), 2.5 (m, 2H), 3.7 (s, 3H), 3.8 (d, 2H), 4.9 (s, 1H), 5.6 (m, 2H), 7.3 (m, 5H), 8.2 (s, 2H) HRMS calcd. For C$_{10}$H$_{19}$N$_3$O$_2$: m/z=214.1550 [M+H]. Found: 214.1544

EXAMPLE 9

A sample of the product from Example 9g (8 g, 20.4 mmol) was dissolved in 6N HCl (100 mL) and was refluxed for 3 h. The solution was concentrated in vacuo to give the amino acid, which was purified on a Dowex 50WX4-200 H form ion exchange resin. The resin (120 g) was washed with 25% HCl followed by H$_2$O to bring to pH 6. The compound was applied in water. The resin was washed successively with 0, 1.7, 3.3, 5, 6.6 and 8.3% HCl. The product started to elute at 5% HCl. The fractions were pooled, and concentrated in vacuo to give the title product as the di-HCl salt (4.3 g, 84%).

Elemental analyses Calcd for C$_9$H$_{17}$N$_3$O$_2$ with 2.1 HCl and 0.1 H$_2$O: C, 38.94; H, 7.01; N, 15.14; Cl, 26.82. Found: C, 38.68; H, 7.17; N, 14.74; Cl, 27.28 $^1$H NMR (300 MHz, D$_2$O, δ ppm): 1.5 (s, 3H), 2.1 (s, 3H), 2.5 (dd, 1H), 2.6 (dd, 1H), 5.6 (m, 2H) HRMS calcd. For C$_9$H$_{17}$N$_3$O$_2$: m/z=200.1394 [M+H]. Found: 200.1371 [α]$_{25}$ in H$_2$O: +17.3 at 365

EXAMPLE 10

(2S,4E)-2-amino-2-methyl-6-(3-methyl-5-oxo-1,2,4-oxadiazol-4(5H)-yl)hex-4-enoic acid hydrochloride

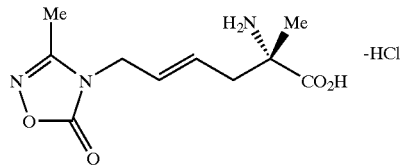

A sample of the product from Example 9e (0.5 g, 1.23 mmol) was dissolved in 3N HCl (50 mL) and was refluxed for 4 h. The solution was concentrated in vacuo to give the amino acid, which was purified on a Dowex 50WX4-200 H form ion exchange resin. The resin (10 g) was washed with 100 mL of 25% HCl followed by 300 mL of H$_2$O to bring to pH 6. The compound was applied in water, followed by 50 mL of water. The resin was washed successively with 1.7, 3.3, 5, 6.6 and 8.3% HCl. The product started to elute at 5% HCl. The fractions were pooled, and concentrated in vacuo to give the title product as the di-HCl salt (264 mg, 88%).

Elemental analyses Calcd for C$_{10}$H$_{15}$N$_3$O$_4$ with 1.1 HCl and 0.5 H$_2$O: C, 41.37; H, 5.94; N, 14.47, Cl, 13.43. Found: C, 41.41; H, 6.14; N, 14.88; Cl, 13.14 $^1$H NMR (300 MHz, D$_2$O, δ ppm): 1.4 (s, 3H), 2.1 (s, 3H), 2.5 (ddd, 2H), 4.1 (d, 2H), 5.5–5.6 (m, 2H) HRMS calcd. For C$_{10}$H$_{19}$N$_3$O$_2$: m/z=214.1550 [M+H]. Found: 214.1544

EXAMPLE 11

(2S,5E)-2-amino-6{[(1Z-N-hydroxyl)ethanimidoyl]amino}-2-methyl hex-4-enoic acid

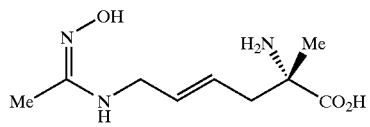

A sample of the product from Example 9e (1.0 g, 2.46 mmol) was converted to the free-base by applying it to a Dowex 50WX4-200 H form and eluting with 5% HCl. The eluent was concentrated in vacuo to give a residue that was dissolved in 2.5 N NaOH (4 mL, 9.84 mmol, 4 equiv) and 4 mL of H₂O. After 4 h, the solution was concentrated and the title product precipitated from cold H₂O (0.215 g).

Elemental analyses Calcd for C₉H₁₇N₃O₃ with 5 NaCl: C, 21.30; H, 3.38; N, 8.28; Cl, 33.93. Found: C, 20.30; H, 3.26; N, 7.70; Cl, 33.46 ¹H NMR (400 MHz, D₂O, δ ppm): 1.3 (s, 3H), 1.8 (s, 3H), 2.4 (m, 2H), 3.7 (d, 2H), 5.4 (m, 1H), 5.6 (m, 1H) HRMS calcd. For C₉H₁₇N₃O₃: m/z=216.1343 [M+H]. Found: 216.1354

Novel Intermediates

Novel intermediates useful in making compounds of the present invention include:

methyl 2-(1,3-dioxo-1,3-dihydro-2H-isoindol-2-yl) propanoate

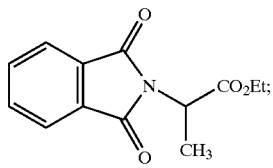

2-[(2E)-4-chlorobut-2-enyl]-1H-isoindole-1,3(2H)-dione

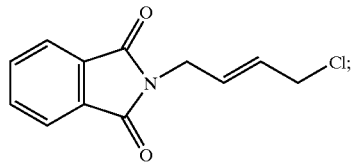

2-[(2E)-4-iodobut-2-enyl]-1H-isoindole-1,3(2H)-dione

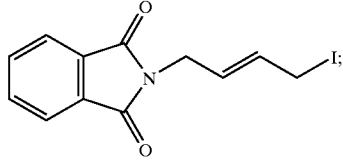

ethyl (4E)-2,6-bis(1,3-dioxo-1,3-dihydro-2H-isoindol-2-yl)-2-methylhex-4-enoate

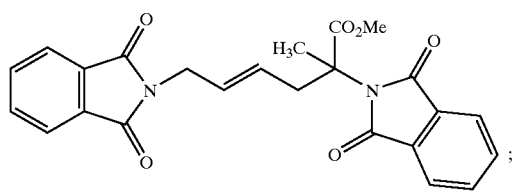

(4E)-2,6-diamino-2-methylhex-4-enoic acid, dihydrochloride

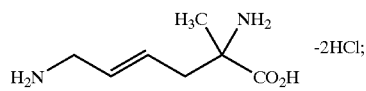

2-{(3E)-5-[(2S,4R)-3-benzoyl-2-tert-butyl-4-methyl-5-oxo-1,3-oxazolidin-4-yl]pent-3-enyl}-1H-isoindole-1,3(2H)-dione

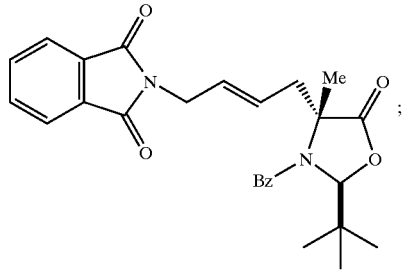

(2R,4E)-2,7-diamino-2-methylhept-4-enoic acid, dihydrochloride

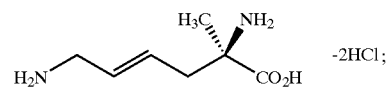

2-{(3E)-5-[(2R,4S)-3-benzoyl-2-tert-butyl-4-methyl-5-oxo-1,3-oxazolidin-4-yl]pent-3-enyl}-1H-isoindole-1,3(2H)-dione

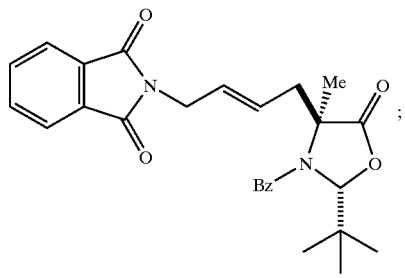

(2S,4E)-2,7-diamino-2-methylhept-4-enoic acid, dihydrochloride

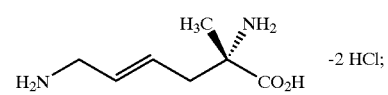

methyl 2-amino-6-[(tert-butoxycarbonyl)amino]-2-methylhex-4-ynoate compound with (1-phenylvinyl)benzene (1:1)

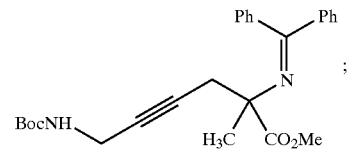

methyl 2,6-diamino-2-methylhex-4-ynoate, dihydrochloride

methyl 2-amino-6-(ethanimidoylamino)-2-methylhex-4-ynoate

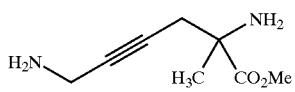 -2HCl;

Potassium salt of 3-methyl-1,2,4-oxadiazol-5(4H)-one

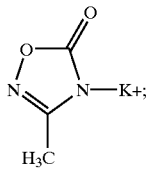

4-[(2E)-4-bromobut-2-enyl]-3-methyl-1,2,4-oxadiazol-5(4H)-one

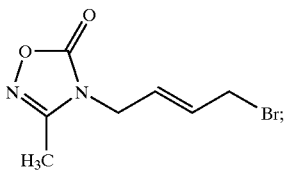

methyl N-(2,6-dichlorobenzylidene)alaninate

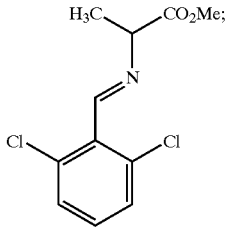

methyl (4E)-2-amino-2-methyl-6-(3-methyl-5-oxo-1,2,4-oxadiazol-4(5H)-yl)hex-4-enoate

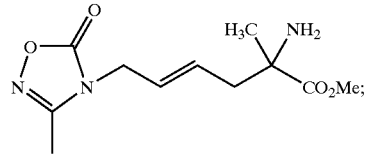

(2S)-hydroxy(phenyl)ethanoic acid salt of methyl (2S,4E)-2-amino-2-methyl-6-(3-methyl-5-oxo-1,2,4-oxadiazol-4(5H)-yl)hex-4-enoate

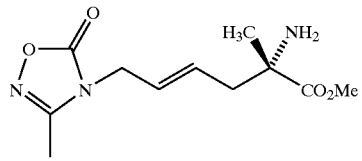

-continued

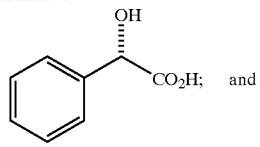 and methyl (S,E)-2-amino-2-methyl-6-[(1-iminoethyl)amino]-4-hexenoate, dihydrochloride

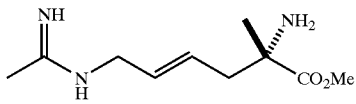 -2HCl.

Biological Data

Some or all of the following assays are used to demonstrate the nitric oxide synthase inhibitory activity of the invention's compounds as well as demonstrate the useful pharmacological properties.

Citrulline Assay for Nitric Oxide Synthase

Nitric oxide synthase (NOS) activity can be measured by monitoring the conversion of L-[2,3-$^3$H]-arginine to L-[2,3-$^3$H]-citrulline (Bredt and Snyder, Proc. Nat. Acad. Sci. U.S.A., 87, 682–685, 1990 and Moore et al, J. Med. Chem., 39, 669–672, 1996). Human inducible NOS (hiNOS), human endothelial constitutive NOS (hecNOS) and human neuronal constitutive NOS (hncNOS) are each cloned from RNA extracted from human tissue. The cDNA for human inducible NOS (hiNOS) is isolated from a λ cDNA library made from RNA extracted from a colon sample from a patient with ulcerative colitis. The cDNA for human endothelial constitutive NOS (hecNOS) is isolated from a λ cDNA library made from RNA extracted from human umbilical vein endothelial cells (HUEC) and the cDNA for human neuronal constitutive NOS (hncNOS) is isolated from a λ cDNA library made from RNA extracted from human cerebellum obtained from a cadaver. The recombinant enzymes are expressed in Sf9 insect cells using a baculovirus vector (Rodi et al, in The Biology of Nitric Oxide, Pt. 4: Enzymology, Biochemistry and Immunology; Moncada, S., Feelisch, M., Busse, R., Higgs, E., Eds.; Portland Press Ltd.: London, 1995; pp 447–450). Enzyme activity is isolated from soluble cell extracts and partially purified by DEAE-Sepharose chromatography. To measure NOS activity, 10 μL of enzyme is added to 40 μL of 50 mM Tris (pH 7.6) in the presence or absence of test compounds and the reaction initiated by the addition of 50 μL of a reaction mixture containing 50 mM Tris (pH 7.6), 2.0 mg/mL bovine serum albumin, 2.0 mM DTT, 4.0 mM $CaCl_2$, 20 μM FAD, 100 μM tetrahydrobiopterin, 0.4 mM NADPH and 60 μM L-arginine containing 0.9 μCi of L-[2,3-$^3$H]-arginine. The final concentration of L-arginine in the assay is 30 μM. For hecNOS or hncNOS, calmodulin is included at a final concentration of 40–100 nM. Following incubation at 37° C. for 15 minutes, the reaction is terminated by addition of 400 μL of a suspension (1 part resin, 3 parts buffer) of Dowex 50W X-8 cation exchange resin (sodium form) in a stop buffer containing 10 mM EGTA, 100 mM HEPES, pH 5.5 and 1 mM L-citrulline. After mixing the resin is allowed to settle and L-[2,3-$^3$H]-Citrulline formation is determined by counting aliquots of the supernatant with a liquid scintillation counter. $IC_{50}$ values can be determined by testing each compound at several concentrations. Results are reported in Table I as the IC$_{50}$ values of compounds for hiNOS, hecNOS and hncNOS.

TABLE I

| Example | IC$_{50}$ [μM] | | |
|---|---|---|---|
| Number | hiNOS | hecNOS | hncNOS |
| Example 1 | 2.9 | 29 | 9.9 |
| Example 6 | 1.4 | 18 | 5.8 |
| Example 5 | 10 | 74 | 31 |
| Example 7 | 16 | 86 | 45 |

In vivo Assay

Rats can be treated with an intraperitoneal injection of 1–12.5 mg/kg of endotoxin (LPS) to induce systemic expression of inducible nitric oxide synthase, resulting in markedly elevated plasma nitrite/nitrate levels. Compounds are administered orally 0.5–1 hours prior to LPS administration and plasma nitrite/nitrate levels are determined 5 hours following LPS administration. The results can be used to show that the administration of the nitric oxide synthase inhibitors decreases the rise in plasma nitrite/nitrate levels, a reliable indicator of the production of nitric oxide induced by endotoxin. ED$_{50}$ values (mg/kg) for inhibition of the LPS-induced increase in plasma nitrite/nitrate levels are shown in Table II.

TABLE II

ED$_{50}$'s for Examples determined in endotoxin-treated rats
All compounds administered orally unless otherwise noted.

| Example No. | ED$_{50}$ (mg/kg) |
|---|---|
| Example 1 | <3 |
| Example 6 | 0.2 |

Raw Cell Nitrite Assay

RAW 264.7 cells can be plated to confluency on a 96-well tissue culture plate grown overnight (17 h) in the presence of LPS to induce NOS. A row of 3–6 wells can be left untreated and serve as controls for subtraction of nonspecific background. The media can be removed from each well and the cells washed twice with Kreb-Ringers-Hepes (25 mM, pH 7.4) with 2 mg/ml glucose. The cells are then placed on ice and incubated with 50 μL of buffer containing L-arginine (30 μM) +/− inhibitors for 1 h. The assay can be initiated by warming the plate to 37° C. in a water bath for 1 h. Production of nitrite by intracellular iNOS will be linear with time. To terminate the cellular assay, the plate of cells can be placed on ice and the nitrite-containing buffer removed and analyzed for nitrite using a previously published fluorescent determination for nitrite (T. P. Misko et al, *Analytical Biochemistry*, 214, 11–16, 1993).

Human Cartilage Explant Assay

Bone pieces are rinsed twice with Dulbecco's Phosphate Buffered Saline (GibcoBRL) and once with Dulbecco's Modified Eagles Medium (GibcoBRL) and placed into a petri dish with phenol red free Minimum Essential Medium (MEM) (GibcoBRL). Cartilage was cut into small explants of approximately 15–45 mg in weight and one or two explants per well are placed into either 96 or 48 well culture plates with 200–500 μL of culture media per well. The culture media was either a custom modification of Minimum Essential Medium(Eagle) with Earle's salts (GibcoBRL) prepared without L-Arginine, without L-Glutamine and without phenol red or a custom modification of serumless Neuman and Tytell (GibcoBRL) medium prepared without L-arginine, without insulin, without ascorbic acid, without L-glutamine and without phenol red. Both are supplemented before use with 100 μM L-Arginine (Sigma), 2 mM L-glutamine, 1×HL-1 supplement (BioWhittaker), 50 mg/ml ascorbic acid (Sigma) and 150 pg/ml recombinant human IL-1β (RD Systems) to induce nitric oxide synthase. Compounds are then added in 10 μL aliquots and the explants incubated at 37° C. with 5% CO$_2$ for 18–24 hours.

The day old supernatant is then discarded and replaced with fresh culture media containing recombinant human IL-1β and compound and incubated for another 20–24 hours. This supernatant is analyzed for nitrite with a fluorometric assay (Misko et al, *Anal. Biochem.*, 214, 11–16, 1993). All samples are done in quadruplicate. Unstimulated controls are cultured in media in the absence of recombinant human IL-1β. IC$_{50}$ values (Table III) are determined from plotting the percent inhibition of nitrite production at six different concentrations of inhibitor.

TABLE III

| Example No. | IC$_{50}$ [μM] |
|---|---|
| Example 1 | 0.5 |
| Example 6 | 0.5 |
| Example 5 | 1.8 |

Assay for Time Dependent Inhibition

Compounds are evaluated for time dependent inhibition of human NOS isoforms by preincubation of the compound with the enzyme at 37° C. in the presence of the citrulline enzyme assay components, minus L-arginine, for times ranging from 0–60 minutes. Aliquots (10 μL) are removed at 0, 10, 21 and 60 minutes and immediately added to a citrulline assay enzyme reaction mixture containing L-[2,3-$^3$H]-arginine and a final L-arginine concentration of 30 μM in a final volume of 100 μL. The reaction is allowed to proceed for 15 minutes at 37° C. and terminated by addition of a suspension of Dowex 50W X-8 cation exchange resin as described above for the citrulline NOS assay. The % inhibition of NOS activity by an inhibitor is taken as the per cent inhibition in activity compared to control enzyme preincubated for the same time in the absence of inhibitor. Time-dependent inhibition can be demonstrated as an increase in inhibition with increasing preincubation time.

What is claimed is :

1. A compound of Formula I:

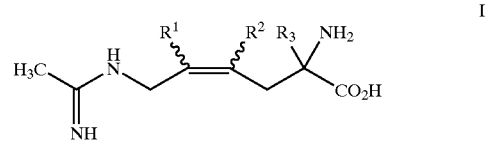

or a pharmaceutically acceptable salt thereof, wherein:
R$^1$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo;
R$^2$ is selected from the group consisting of hydrogen, halo, and C$_1$–C$_5$ alkyl, said C$_1$–C$_5$ alkyl optionally substituted by halo or alkoxy, said alkoxy optionally substituted by one or more halo; and
R$^3$ is C$_1$–C$_5$ alkyl, said C$_1$–C$_5$ alkyl optionally substituted by halo or alkoxy, said alkoxy optionally substituted by one or more halo.

2. The compound of claim 1 wherein the compound is the Z isomer.

3. The compound of claim 2 wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by halo or alkoxy.

4. The compound of claim 3 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_5$ alkyl, said $C_1$–$C_5$ alkyl optionally substituted by halo or alkoxy.

5. The compound of claim 3 wherein:
$R^1$ is selected from the group consisting of hydrogen, halo, and $C_1$–$C_5$ alkyl; said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl; and
$R^3$ is $C_1$–$C_5$ alkyl, said $C_1$–$C_5$ alkyl optionally substituted by fluorine or alkoxy.

6. The compound of claim 3 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl optionally substituted by fluorine.

7. The compound of claim 3 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl.

8. The compound of claim 3 wherein:
$R^1$ is hydrogen;
$R^2$ is selected from the group consisting of hydrogen, halo and $C_1$–$C_3$ alkyl; and
$R^3$ is $C_1$–$C_3$ alkyl.

9. The compound of claim 8 wherein:
$R^1$ is hydrogen;
$R^2$ is selected from the group consisting of hydrogen and halo; and
$R^3$ is $C_1$–$C_3$ alkyl.

10. The compound of claim 9 wherein:
$R^1$ is hydrogen;
$R^2$ is selected from the group consisting of hydrogen and fluorine; and
$R^3$ is $C_1$–$C_3$ alkyl.

11. The compound of claim 10 wherein:
$R^1$ is hydrogen;
$R^2$ is selected from the group consisting of hydrogen and fluorine; and
$R^3$ is methyl.

12. The compound of claim 11 wherein:
$R^1$ is hydrogen;
$R^2$ is hydrogen; and
$R^3$ is methyl.

13. The compound of claim 11 wherein:
$R^1$ is hydrogen;
$R^2$ is fluorine; and
$R^3$ is methyl.

14. The compound of claim 3 wherein:
$R^1$ is halo;
$R^2$ is selected from the group consisting of hydrogen, halo and $C_1$–$C_3$ alkyl; and
$R^3$ is $C_1$–$C_3$ alkyl.

15. The compound of claim 14 wherein:
$R^1$ is halo;
$R^2$ is halo; and
$R^3$ is $C_1$–$C_3$ alkyl.

16. The compound of claim 15 wherein:
$R^1$ is fluorine;
$R^2$ is fluorine; and
$R^3$ is methyl.

17. The compound of claim 14 wherein:
$R^1$ is fluorine;
$R^2$ is selected from the group consisting of hydrogen and $C_1$–$C_3$ alkyl; and
$R^3$ is methyl.

18. The compound of claim 17 wherein:
$R^1$ is fluorine;
$R^2$ is hydrogen; and
$R^3$ is methyl.

19. The compound of claim 3 wherein:
$R^1$ is methyl;
$R^2$ is hydrogen; and
$R^3$ is methyl.

20. The compound of claim 3 wherein:
$R^1$ is hydrogen;
$R^2$ is methyl; and
$R^3$ is methyl.

21. The compound of claim 3 wherein:
$R^1$ is methyl;
$R^2$ is methyl; and
$R^3$ is methyl.

22. The compound of claim 2 wherein:
$R^1$ is selected from the group consisting of hydrogen, halo and $C_1$–$C_5$ alkyl, said $C_1$–$C_5$ alkyl optionally substituted by alkoxy or one or more fluorine;
$R^2$ is selected from the group consisting of hydrogen, halo and $C_1$–$C_5$ alkyl, said $C_1$–$C_5$ alkyl optionally substituted by alkoxy or one or more fluorine; and
$R^3$ is methyl optionally substituted by one or more alkoxy or halo.

23. The compound of claim 22 wherein:
$R^1$ is selected from the group consisting of hydrogen and fluorine;
$R^2$ is $C_1$–$C_3$ alkyl substituted by one or more halo; and
$R^3$ methyl.

24. The compound of claim 23 wherein:
$R^1$ is hydrogen;
$R^2$ is $CH_2F$; and
$R^3$ is methyl.

25. The compound of claim 22 wherein:
$R^1$ is $CH_2F$;
$R^2$ is hydrogen; and
$R^3$ is methyl.

26. The compound of claim 22 wherein:
$R^1$ is hydrogen;
$R^2$ is hydrogen; and
$R^3$ is $CH_2F$.

27. The compound of claim 22 wherein:
$R^1$ is hydrogen;
$R^2$ is methoxymethyl; and
$R^3$ is methyl.

28. The compound of claim 22 wherein:
$R^1$ is methoxymethyl;
$R^2$ hydrogen; and
$R^3$ is methyl.

29. The compound of claim 22 wherein:
$R^1$ is hydrogen;
$R^2$ is hydrogen; and
$R^3$ is methoxymethyl.

30. The compound of claim 1 wherein the compound is the E isomer.

31. The compound of claim 30 wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^1$ is selected from the group consisting of hydrogen, halo and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by one or more halo or alkoxy.

32. The compound of claim 31 wherein:
$R^1$ is selected from the group consisting of hydrogen, halo, and $C_1$–$C_5$ alkyl; said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl; and
$R^3$ is $C_1$–$C_5$ alkyl, said $C_1$–$C_5$ alkyl optionally substituted by halo or alkoxy.

33. The compound of claim 31 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl optionally substituted by fluorine.

34. The compound of claim 31 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_5$ alkyl, said $C_1$–$C_5$ alkyl optionally substituted by fluorine or alkoxy.

35. The compound of claim 31 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl.

36. The compound of claim 31 wherein:
$R^1$ is hydrogen;
$R^2$ is selected from the group consisting of hydrogen, halo and $C_1$–$C_3$ alkyl; and
$R^3$ is $C_1$–$C_3$ alkyl.

37. The compound of claim 36 wherein:
$R^1$ is hydrogen;
$R^2$ is selected from the group consisting of hydrogen and halo; and
$R^3$ is $C_1$–$C_3$ alkyl.

38. The compound of claim 37 wherein:
$R^1$ is hydrogen;
$R^2$ is selected from the group consisting of hydrogen and fluorine; and
$R^3$ is $C_1$–$C_3$ alkyl.

39. The compound of claim 38 wherein:
$R^1$ is hydrogen;
$R^2$ is selected from the group consisting of hydrogen and fluorine; and
$R^3$ is methyl.

40. The compound of claim 39 wherein:
$R^1$ is hydrogen;
$R^2$ is hydrogen; and
$R^3$ is methyl.

41. The compound of claim 39 wherein:
$R^1$ is hydrogen;
$R^2$ is fluorine; and
$R^3$ is methyl.

42. The compound of claim 31 wherein:
$R^1$ is halo;
$R^2$ is selected from the group consisting of hydrogen, halo and $C_1$–$C_3$ alkyl; and
$R^3$ is $C_1$–$C_3$ alkyl.

43. The compound of claim 42 wherein:
$R^1$ is halo;
$R^2$ is halo; and
$R^3$ is $C_1$–$C_3$ alkyl.

44. The compound of claim 43 wherein:
$R^1$ is fluorine;
$R^2$ is fluorine; and
$R^3$ is methyl.

45. The compound of claim 42 wherein:
$R^1$ is fluorine;
$R^2$ is selected from the group consisting of hydrogen and $C_1$–$C_3$ alkyl; and
$R^3$ is methyl.

46. The compound of claim 45 wherein:
$R^1$ is fluorine;
$R^2$ is hydrogen; and
$R^3$ is methyl.

47. The compound of claim 31 wherein:
$R^1$ is methyl;
$R^2$ is hydrogen; and
$R^3$ is methyl.

48. The compound of claim 31 wherein:
$R^1$ is hydrogen;
$R^2$ is methyl; and
$R^3$ is methyl.

49. The compound of claim 31 wherein:
$R^1$ is methyl;
$R^2$ is methyl; and
$R^3$ is methyl.

50. The compound of claim 30 wherein:
$R^1$ is selected from the group consisting of hydrogen, halo and $C_1$–$C_5$ alkyl, said $C_1$–$C_5$ alkyl optionally substituted by alkoxy or one or more fluorine;

$R^2$ is selected from the group consisting of hydrogen, halo and $C_1$–$C_5$ alkyl, said $C_1$–$C_5$ alkyl optionally substituted by alkoxy or one or more fluorine; and $R^3$ is methyl optionally substituted by alkoxy or one or more halo.

51. The compound of claim 50 wherein:
$R^1$ is selected from the group consisting of hydrogen and fluorine;
$R^2$ is $C_1$–$C_3$ alkyl substituted by one or more halo; and
$R^3$ is methyl.

52. The compound of claim 51 wherein:
$R^1$ is hydrogen;
$R^2$ is $CH_2F$; and
$R^3$ is methyl.

53. The compound of claim 50 wherein:
$R^1$ is $CH_2F$;
$R^2$ is hydrogen; and
$R^3$ is methyl.

54. The compound of claim 50 wherein:
$R^1$ is hydrogen;
$R^2$ is hydrogen; and
$R^3$ is $CH_2F$.

55. The compound of claim 50 wherein:
$R^1$ is hydrogen;
$R^2$ is methoxymethyl; and
$R^3$ is methyl.

56. The compound of claim 50 wherein:
$R^1$ is methoxymethyl;
$R^2$ is hydrogen; and
$R^3$ is methyl.

57. The compound of claim 50 wherein:
$R^1$ is hydrogen;
$R^2$ is hydrogen; and
$R^3$ is methoxymethyl.

58. A compound of Formula II

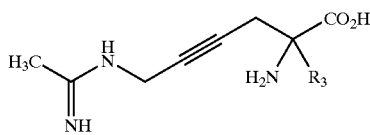

II or a pharmaceutically acceptable salt thereof, wherein:
$R^3$ is $C_1$–$C_5$ alkyl, said $C_1$–$C_5$ alkyl optionally substituted by halo or alkoxy, said alkoxy optionally substituted by one or more halo.

59. The compound of claim 58 wherein:
$R^3$ is $C_1$–$C_5$ alkyl substituted by one or more halo.

60. The compound of claim 59 wherein:
$R^3$ is $C_1$–$C_5$ alkyl substituted by one or more fluorine.

61. The compound of claim 59 wherein:
$R^3$ methyl substituted by one or more halo.

62. The compound of claim 61 wherein:
$R^3$ is methyl substituted by one or more fluorine.

63. The compound of claim 61 wherein:
$R^3$ is $CH_2F$.

64. The compound of claim 58 wherein:
$R^3$ is $C_1$–$C_5$ alkyl substituted by alkoxy.

65. The compound of claim 64 wherein:
$R^3$ is methoxy methyl.

66. The compound of claim 58 wherein:
$R^3$ is $C_1$–$C_5$ alkyl.

67. The compound of claim 66 wherein:
$R^3$ is methyl.

68. A compound of Formula III

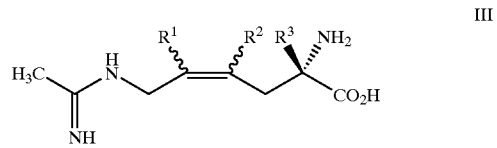

III or a pharmaceutically acceptable salt thereof, wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by halo or alkoxy, said alkoxy optionally substituted by one or more halo.

69. The compound of claim 68 wherein the compound is the Z isomer.

70. The compound of claim 69 wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by one or more halo or alkoxy.

71. The compound of claim 69 wherein:
$R^1$ is selected from the group consisting of hydrogen, halo, and $C_1$–$C_5$ alkyl; said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl; and
$R^3$ is $C_1$–$C_5$ alkyl, said $C_{1-C5}$ alkyl optionally substituted by halo or alkoxy.

72. The compound of claim 69 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl optionally substituted by fluorine.

73. The compound of claim 70 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_5$ alkyl, said $C_1$–$C_5$ alkyl optionally substituted by fluorine or alkoxy.

74. The compound of claim 70 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl.

75. The compound of claim 70 wherein:
$R^1$ is hydrogen;
$R^2$ is selected from the group consisting of hydrogen, halo and $C_1$–$C_3$ alkyl; and
$R^3$ is $C_1$–$C_3$ alkyl.

76. The compound of claim 75 wherein:
$R^1$ is hydrogen;
$R^2$ is selected from the group consisting of hydrogen and halo; and
$R^3$ is $C_1$–$C_3$ alkyl.

77. The compound of claim 76 wherein:
$R^1$ is hydrogen;
$R^2$ is selected from the group consisting of hydrogen and fluorine; and
$R^3$ is $C_1$–$C_3$ alkyl.

78. The compound of claim 77 wherein:
$R^1$ is hydrogen;
$R^2$ is selected from the group consisting of hydrogen and fluorine; and
$R^3$ is methyl.

79. The compound of claim 78 wherein:
$R^1$ is hydrogen;
$R^2$ is hydrogen; and
$R^3$ is methyl.

80. The compound of claim 78 wherein:
$R^1$ is hydrogen;
$R^2$ is fluorine; and
$R^3$ is methyl.

81. The compound of claim 70 wherein:
$R^1$ is halo;
$R^2$ is selected from the group consisting of hydrogen, halo and $C_1$–$C_3$ alkyl; and
$R^3$ is $C_1$–$C_3$ alkyl.

82. The compound of claim 81 wherein:
$R^1$ is halo;
$R^2$ is halo; and
$R^3$ is $C_1$–$C_3$ alkyl.

83. The compound of claim 82 wherein:
$R^1$ is fluorine;
$R^2$ is fluorine; and
$R^3$ is methyl.

84. The compound of claim 81 wherein:
$R^1$ is fluorine;
$R^2$ is selected from the group consisting of hydrogen and $C_1$–$C_3$ alkyl; and
$R^3$ is methyl.

85. The compound of claim 84 wherein:
$R^1$ is fluorine;
$R^2$ is hydrogen; and
$R^3$ is methyl.

86. The compound of claim 70 wherein:
$R^1$ is methyl;
$R^2$ is hydrogen; and
$R^3$ is methyl.

87. The compound of claim 70 wherein:
$R^1$ is hydrogen;
$R^2$ is methyl; and
$R^3$ is methyl.

88. The compound of claim 70 wherein:
$R^1$ is methyl;
$R^2$ is methyl; and
$R^3$ is methyl.

89. The compound of claim 69 wherein:
$R^1$ is selected from the group consisting of hydrogen, halo and $C_1$–$C_5$ alkyl, said $C_1$–$C_5$ alkyl optionally substituted by alkoxy or one or more fluorine;
$R^2$ is selected from the group consisting of hydrogen, halo and $C_1$–$C_5$ alkyl, said $C_1$–$C_5$ alkyl optionally substituted by alkoxy or one or more fluorine; and
$R^3$ is methyl optionally substituted by one or more alkoxy or halo.

90. The compound of claim 89 wherein:
$R^1$ is selected from the group consisting of hydrogen and fluorine;
$R^2$ is $C_1$–$C_3$ alkyl substituted by one or more halo; and
$R^3$ is methyl.

91. The compound of claim 90 wherein:
$R^1$ is hydrogen;
$R^2$ is $CH_2F$; and
$R^3$ is methyl.

92. The compound of claim 89 wherein:
$R^1$ is $CH_2F$;
$R^2$ is hydrogen; and
$R^3$ is methyl.

93. The compound of claim 89 wherein:
$R^1$ is hydrogen;
$R^2$ is hydrogen; and
$R^3$ is $CH_2F$.

94. The compound of claim 89 wherein:
$R^1$ is hydrogen;
$R^2$ is methoxymethyl; and
$R^3$ is methyl.

95. The compound of claim 89 wherein:
$R^1$ is methoxymethyl;
$R^2$ is hydrogen; and
$R^3$ is methyl.

96. The compound of claim 89 wherein:
$R^1$ is hydrogen;
$R^2$ is hydrogen; and
$R^3$ is methoxymethyl.

97. The compound of claim 68 wherein the compound is the E isomer.

98. The compound of claim 97 wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by one or more halo or alkoxy.

99. The compound of claim 98 wherein:
$R^1$ is selected from the group consisting of hydrogen, halo, and $C_1$–$C_5$ alkyl; said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl; and
$R^3$ is $C_1$–$C_5$ alkyl, said $C_1$–$C_5$ alkyl optionally substituted by halo or alkoxy.

100. The compound of claim 98 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl optionally substituted by fluorine.

101. The compound of claim 98 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_5$ alkyl, said $C_1$–$C_5$ alkyl optionally substituted by one or more fluorine or alkoxy.

102. The compound of claim 98 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl.

103. The compound of claim 98 wherein:
$R^1$ is hydrogen;
$R^2$ is selected from the group consisting of hydrogen, halo and $C_1$–$C_3$ alkyl; and
$R^3$ is $C_1$–$C_3$ alkyl.

104. The compound of claim 103 wherein:
$R^1$ is hydrogen;
$R^2$ is selected from the group consisting of hydrogen and halo; and
$R^3$ is $C_1$–$C_3$ alkyl.

105. The compound of claim 104 wherein:
$R^1$ is hydrogen;
$R^2$ is selected from the group consisting of hydrogen and fluorine; and
$R^3$ is $C_1$–$C_3$ alkyl.

106. The compound of claim 105 wherein:
$R^1$ is hydrogen;
$R^2$ is selected from the group consisting of hydrogen and fluorine; and
$R^3$ is methyl.

107. The compound of claim 106 wherein:
$R^1$ is hydrogen;
$R^2$ is hydrogen; and
$R^3$ is methyl.

108. The compound of claim 106 wherein:
$R^1$ is hydrogen;
$R^2$ is fluorine; and
$R^3$ is methyl.

109. The compound of claim 98 wherein:
$R^1$ is halo;
$R^2$ is selected from the group consisting of hydrogen, halo and $C_1$–$C_3$ alkyl; and
$R^3$ is $C_1$–$C_3$ alkyl.

110. The compound of claim 109 wherein:
$R^1$ is halo;
$R^2$ is halo; and
$R^3$ is $C_1$–$C_3$ alkyl.

111. The compound of claim 110 wherein:
$R^1$ is fluorine;
$R^2$ is fluorine; and
$R^3$ is methyl.

112. The compound of claim 109 wherein:
$R^1$ is fluorine;
$R^2$ is selected from the group consisting of hydrogen and $C_1$–$C_3$ alkyl; and
$R^3$ is methyl.

113. The compound of claim 112 wherein:
$R^1$ is fluorine;
$R^2$ is hydrogen; and
$R^3$ is methyl.

114. The compound of claim 98 wherein:
$R^1$ is methyl;
$R^2$ is hydrogen; and
$R^3$ is methyl.

115. The compound of claim 98 wherein:
$R^1$ is hydrogen;
$R^2$ is methyl; and
$R^3$ is methyl.

116. The compound of claim 98 wherein:
$R^1$ is methyl;
$R^2$ is methyl; and
$R^3$ is methyl.

117. The compound of claim 97 wherein:
$R^1$ is selected from the group consisting of hydrogen, halo and $C_1$–$C_5$ alkyl, said $C_1$–$C_5$ alkyl optionally substituted by alkoxy or one or more fluorine;
$R^2$ is selected from the group consisting of hydrogen, halo and $C_1$–$C_5$ alkyl, said $C_1$–$C_5$ alkyl optionally substituted by alkoxy or one or more fluorine; and
$R^3$ is methyl optionally substituted by one or more alkoxy or halo.

118. The compound of claim 117 wherein:
$R^1$ is selected from the group consisting of hydrogen and fluorine;
$R^2$ is $C_1$–$C_3$ alkyl substituted by one or more halo; and
$R^3$ is methyl.

119. The compound of claim 118 wherein:
$R^1$ is hydrogen;
$R^2$ is $CH_2F$; and
$R^3$ is methyl.

120. The compound of claim 117 wherein:
$R^1$ is $CH_2F$;
$R^2$ is hydrogen; and
$R^3$ is methyl.

121. The compound of claim 117 wherein:
$R^1$ is hydrogen;
$R^2$ is hydrogen; and
$R^3$ is $CH_2F$.

122. The compound of claim 117 wherein:
$R^1$ is hydrogen;
$R^2$ is methoxymethyl; and
$R^3$ is methyl.

123. The compound of claim 117 wherein:
$R^1$ is methoxymethyl;
$R^2$ is hydrogen; and
$R^3$ is methyl.

124. The compound of claim 117 wherein:
$R^1$ is hydrogen;
$R^2$ is hydrogen; and
$R^3$ is methoxymethyl.

125. A compound of Formula IV

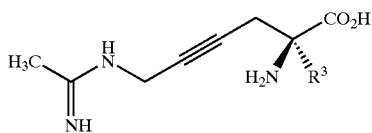

or a pharmaceutically acceptable salt thereof, wherein:
$R^3$ is $C_1$–$C_5$ alkyl, said $C_1$–$C_5$ alkyl optionally substituted by halo or alkoxy, said alkoxy optionally substituted by one or more halo.

126. The compound of claim 125 wherein:
$R^3$ is $C_1$–$C_5$ alkyl substituted by one or more halo.

127. The compound of claim 126 wherein:
$R^3$ is $C_1$–$C_5$ alkyl substituted by one or more fluorine.

128. The compound of claim 126 wherein:
$R^3$ methyl substituted by one or more halo.

129. The compound of claim 128 wherein:
$R^3$ is methyl substituted by one or more fluorine.

130. The compound of claim 128 wherein:
$R^3$ is $CH_2F$.

131. The compound recited in claim 125 wherein:
$R^3$ is $C_1$–$C_5$ alkyl substituted by alkoxy.

132. The compound of claim 131 wherein:
$R^3$ is methoxy methyl.

133. The compound of claim 125 wherein:
$R^3$ is $C_1$–$C_5$ alkyl.

134. The compound of claim 133 wherein:
$R^3$ is methyl.

135. A compound of Formula V

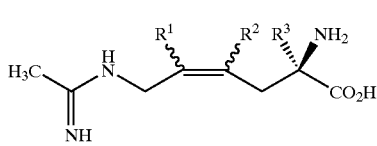

or a pharmaceutically acceptable salt thereof, wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by halo or alkoxy, said alkoxy optionally substituted by one or more halo.

136. The compound of claim 135 wherein the compound is the Z isomer.

137. The compound of claim 136 wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by halo or alkoxy.

138. The compound of claim 137 wherein:
$R^1$ is selected from the group consisting of hydrogen, halo, and $C_1$–$C_5$ alkyl; said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl; and
$R^3$ is $C_1$–$C_5$ alkyl, said $C_1$–$C_5$ alkyl optionally substituted by halo or alkoxy.

139. The compound of claim 137 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl optionally substituted by fluorine.

140. The compound of claim 136 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_5$ alkyl, said $C_1$–$C_5$ alkyl optionally substituted by fluorine or alkoxy.

141. The compound of claim 137 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl.

142. The compound of claim 137 wherein:
$R^1$ is hydrogen;
$R^2$ is selected from the group consisting of hydrogen, halo and $C_1$–$C_3$ alkyl; and
$R^3$ is $C_1$–$C_3$ alkyl.

143. The compound of claim 142 wherein:
$R^1$ is hydrogen;
$R^2$ is selected from the group consisting of hydrogen and halo; and
$R^3$ is $C_1$–$C_3$ alkyl.

144. The compound of claim 143 wherein:
$R^1$ is hydrogen;
$R^2$ is selected from the group consisting of hydrogen and fluorine; and
$R^3$ is $C_1$–$C_3$ alkyl.

145. The compound of claim 144 wherein:
$R^1$ is hydrogen;
$R^2$ is selected from the group consisting of hydrogen and fluorine; and
$R^3$ is methyl.

146. The compound of claim 145 wherein:
$R^1$ is hydrogen;
$R^2$ is hydrogen; and
$R^3$ is methyl.

147. The compound of claim 145 wherein:
$R^1$ is hydrogen;
$R^2$ is fluorine; and
$R^3$ is methyl.

148. The compound of claim 137 wherein:
$R^1$ is halo;
$R^2$ is selected from the group consisting of hydrogen, halo and $C_1$–$C_3$ alkyl; and
$R^3$ is $C_1$–$C_3$ alkyl.

149. The compound of claim 148 wherein:
$R^1$ is halo;
$R^2$ is halo; and
$R^3$ is $C_1$–$C_3$ alkyl.
150. The compound of claim 149 wherein:
$R^1$ is fluorine;
$R^2$ is fluorine; and
$R^3$ is methyl.
151. The compound of claim 148 wherein:
$R^1$ is fluorine;
$R^2$ is selected from the group consisting of hydrogen and $C_1$–$C_3$ alkyl; and
$R^3$ is methyl.
152. The compound of claim 151 wherein:
$R^1$ is fluorine;
$R^2$ is hydrogen; and
$R^3$ is methyl.
153. The compound of claim 137 wherein:
$R^1$ is methyl;
$R^2$ is hydrogen; and
$R^3$ is methyl.
154. The compound of claim 137 wherein:
$R^1$ is hydrogen;
$R^2$ is methyl; and
$R^3$ is methyl.
155. The compound of claim 137 wherein:
$R^1$ is methyl;
$R^2$ is methyl; and
$R^3$ is methyl.
156. The compound of claim 136 wherein:
$R^1$ is selected from the group consisting of hydrogen, halo and $C_1$–$C_5$ alkyl, said $C_1$–$C_5$ alkyl optionally substituted by alkoxy or one or more fluorine;
$R^2$ is selected from the group consisting of hydrogen, halo and $C_1$–$C_5$ alkyl, said $C_1$–$C_5$ alkyl optionally substituted by alkoxy or one or more fluorine; and
$R^3$ is $C_1$–$C_5$ alkyl optionally substituted by alkoxy or one or more halo.
157. The compound of claim 156 wherein:
$R^1$ is selected from the group consisting of hydrogen and fluorine;
$R^2$ is $C_1$–$C_3$ alkyl substituted by one or more halo; and
$R^3$ is methyl.
158. The compound of claim 157 wherein:
$R^1$ is hydrogen;
$R^2$ is $CH_2F$; and
$R^3$ is methyl.
159. The compound of claim 156 wherein:
$R^1$ is $CH_2F$;
$R^2$ is hydrogen; and
$R^3$ is methyl.
160. The compound of claim 156 wherein:
$R^1$ is hydrogen;
$R^2$ is hydrogen; and
$R^3$ is $CH_2F$.
161. The compound of claim 156 wherein:
$R^1$ is hydrogen;
$R^2$ is methoxymethyl; and
$R^3$ is methyl.
162. The compound of claim 156 wherein:
$R^1$ is methoxymethyl;
$R^2$ is hydrogen; and
$R^3$ is methyl.
163. The compound of claim 156 wherein:
$R^1$ is hydrogen;
$R^2$ is hydrogen; and
$R^3$ is methoxymethyl.
164. The compound of claim 135 wherein the compound is the E isomer.
165. The compound of claim 164 wherein:
$R^1$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl, said $C_1$–$C_5$ alkyl optionally substituted by halo or alkoxy, said alkoxy optionally substituted by one or more halo; and
$R^3$ is $C_1$–$C_5$ alkyl, said $C_1$–$C_5$ alkyl optionally substituted by one or more halo or alkoxy.
166. The compound of claim 165 wherein:
$R^1$ is selected from the group consisting of hydrogen, and $C_1$–$C_5$ alkyl; said $C_1$–$C_5$ alkyl optionally substituted by halo or alkoxy, said alkoxy optionally substituted by one or more halo;
$R^2$ is selected from the group consisting of hydrogen, halo and $C_1$–$C_5$ alkyl; and
$R^3$ is $C_1$–$C_5$ alkyl, said $C_1$–$C_5$ alkyl optionally substituted by halo or alkoxy.
167. The compound of claim 165 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl optionally substituted by fluorine.
168. The compound of claim 165 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_5$ alkyl, said $C_1$–$C_5$ alkyl optionally substituted by fluorine or alkoxy.
169. The compound of claim 165 wherein:
$R^1$ is selected from the group consisting of hydrogen, halo, and $C_1$–$C_3$ alkyl;
$R^2$ is selected from the group consisting of hydrogen, halo and $C_1$–$C_3$ alkyl; and
$R^3$ is $C_1$–$C_3$ alkyl.
170. The compound of claim 165 wherein:
$R^1$ is hydrogen;
$R^2$ is selected from the group consisting of hydrogen, halo and $C_1$–$C_3$ alkyl; and
$R^3$ is $C_1$–$C_3$ alkyl.
171. The compound of claim 170 wherein:
$R^1$ is hydrogen;
$R^2$ is selected from the group consisting of hydrogen and halo; and
$R^3$ is $C_1$–$C_3$ alkyl.

172. The compound of claim 171 wherein:
$R^1$ is hydrogen;
$R^2$ is selected from the group consisting of hydrogen and fluorine; and
$R^3$ is $C_1$–$C_3$ alkyl.
173. The compound of claim 172 wherein:
$R^1$ is hydrogen;
$R^2$ is selected from the group consisting of hydrogen and fluorine; and
$R^3$ is methyl.
174. The compound of claim 172 wherein:
$R^1$ is hydrogen;
$R^2$ is hydrogen; and
$R^3$ is methyl.
175. The compound of claim 173 wherein:
$R^1$ is hydrogen;
$R^2$ is fluorine; and
$R^3$ is methyl.
176. The compound of claim 165 wherein:
$R^1$ is halo;
$R^2$ is selected from the group consisting of hydrogen, halo and $C_1$–$C_3$ alkyl; and
$R^3$ is $C_1$–$C_3$ alkyl.
177. The compound of claim 176 wherein:
$R^1$ is halo;
$R^2$ is halo; and
$R^3$ is $C_1$–$C_3$ alkyl.
178. The compound of claim 177 wherein:
$R^1$ is fluorine;
$R^2$ is fluorine; and
$R^3$ is methyl.
179. The compound of claim 176 wherein:
$R^1$ is fluorine;
$R^2$ is selected from the group consisting of hydrogen and $C_1$–$C_3$ alkyl; and
$R^3$ is methyl.
180. The compound of claim 179 wherein:
$R^1$ is fluorine;
$R^2$ is hydrogen; and
$R^3$ is methyl.
181. The compound of claim 165 wherein:
$R^1$ is methyl;
$R^2$ is hydrogen; and
$R^3$ is methyl.
182. The compound of claim 165 wherein:
$R^1$ is hydrogen;
$R^2$ is methyl; and
$R^3$ is methyl.
183. The compound of claim 165 wherein:
$R^1$ is methyl;
$R^2$ is methyl; and
$R^3$ is methyl.
184. The compound of claim 164 wherein:
$R^1$ is selected from the group consisting of hydrogen, halo and $C_1$–$C_5$ alkyl, said $C_1$–$C_5$ alkyl optionally substituted by alkoxy or one or more fluorine;
$R^2$ is selected from the group consisting of hydrogen, halo and $C_1$–$C_5$ alkyl, said $C_1$–$C_5$ alkyl optionally substituted by alkoxy or one or more fluorine; and
$R^3$ is methyl optionally substituted by one or more alkoxy or halo.
185. The compound of claim 184 wherein:
$R^1$ selected from the group consisting of hydrogen and fluorine;
$R^2$ is $C_1$–$C_3$ alkyl substituted by one or more halo; and
$R^3$ is methyl.
186. The compound of claim 185 wherein:
$R^1$ is hydrogen;
$R^2$ is $CH_2F$; and
$R^3$ is methyl.
187. The compound of claim 185 wherein:
$R^1$ is $CH_2F$;
$R^2$ is hydrogen; and
$R^3$ is methyl.
188. The compound of claim 184 wherein:
$R^1$ is hydrogen;
$R^2$ is hydrogen; and
$R^3$ is $CH_2F$.
189. The compound of claim 184 wherein:
$R^1$ is hydrogen;
$R^2$ is methoxymethyl; and
$R^3$ is methyl.
190. The compound of claim 184 wherein:
$R^1$ is methoxymethyl;
$R^2$ is hydrogen; and
$R^3$ is methyl.
191. The compound of claim 184 wherein:
$R^1$ is hydrogen;
$R^2$ is hydrogen; and
$R^3$ is methoxymethyl.
192. A compound of Formula VI

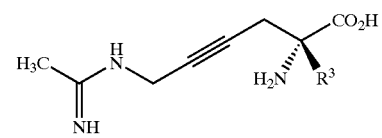

or a pharmaceutically acceptable salt thereof, wherein:
$R^3$ is $C_1$–$C_5$ alkyl, said $C_1$–$C_5$ alkyl optionally substituted by halo or alkoxy, said alkoxy optionally substituted by one or more halo.
193. The compound of claim 192 wherein:
$R^3$ is $C_1$–$C_5$ alkyl substituted by one or more halo.
194. The compound of claim 193 wherein:
$R^3$ is $C_1$–$C_5$ alkyl substituted by one or more fluorine.
195. The compound of claim 193 wherein:
$R^3$ is methyl substituted by one or more halo.
196. The compound of claim 195 wherein:
$R^3$ is methyl substituted by one or more fluorine.
197. The compound of claim 195 wherein:
$R^3$ is $CH_2F$.
198. The compound recited in claim 192 wherein:
$R^3$ is $C_1$–$C_5$ alkyl substituted by alkoxy.
199. The compound of claim 198 wherein:
$R^3$ is methoxy methyl.
200. The compound of claim 192 wherein:
$R^3$ is $C_1$–$C_5$ alkyl.
201. The compound of claim 200 wherein:
$R^3$ is methyl.

202. A compound useful as an intermediate selected from the group consisting of:

ethyl (4E)-2,6-bis(1,3-dioxo-1,3-dihydro-2H-isoindol-2-yl)-2-methylhex-4-enoate;

(4E)-2,6-diamino-2-methylhex-4-enoic acid, dihydrochloride;

2-{(3E)-5-[(2S,4R)-3-benzoyl-2-tert-butyl-4-methyl-5-oxo-1,3-oxazolidin-4-yl]pent-3-enyl}-1H-isoindole-1,3(2H)-dione;

(2R,4E)-2,7-diamino-2-methylhept-4-enoic acid, dihydrochloride;

2-{(3E)-5-[(2R,4S)-3-benzoyl-2-tert-butyl-4-methyl-5-oxo-1,3-oxazolidin-4-yl]pent-3-enyl}-1H-isoindole-1,3(2H)-dione;

(2S,4E)-2,7-diamino-2-methylhept-4-enoic acid, dihydrochloride;

methyl 2-amino-6-[(tert-butoxycarbonyl)amino]-2-methylhex-4-ynoate compound with (1-phenylvinyl)benzene (1:1);

methyl 2,6-diamino-2-methylhex-4-ynoate, dihydrochloride;

methyl 2-amino-6-(ethanimidoylamino-2-methylhex-4-ynoate;

4-[(2E)-4-bromobut-2-enyl]-3-methyl-1,2,4-oxadiazol-5(4H)-one;

methyl N-(2,6-dichlorobenzylidene)alaninate;

(2S)-hydroxy(phenyl)ethanoic acid, formic acid salt of Methyl (S,E)-2-amino-2-methyl-6-[(1-iminoethyl)amino]-4-hexenoate;

(2S)-hydroxy(phenyl)ethanoic acid salt of Methyl (2S,4E)-2-amino-2-methyl-6-(3-methyl-5-oxo-1,2,4-oxadiazol-4(5H)-yl)hex-4-enoate; and Methyl (S,E)-2-amino-2-methyl-6-[(1-iminoethyl)amino]-4-hexenoate, dihydrochloride.

203. A compound selected from the group consisting of:

(E)-2-amino-2-methyl-6-[(1-iminoethyl)amino]-4-hexenoic acid;

(S,E)-2-amino-2-methyl-5-fluoro-6-[(1-iminoethyl)amino]-4-hexenoic acid;

(S,E)-2-amino-2-methyl-4-fluoro-6-[(1-iminoethyl)amino]-4-hexenoic acid;

(S,E)-2-amino-2-methyl-4,5-difluoro-6-[(1-iminoethyl)amino]-4-hexenoic acid;

(R,E)-2-amino-2-methyl-6-[(1-iminoethyl)amino]-4-hexenoic acid;

(S,E)-2-amino-2-methyl-6-[(1-iminoethyl)amino]-4-hexenoic acid;

2-amino-2-methyl-6-[(1-iminoethyl)amino]-4-hexynoic acid;

(Z)-2-amino-2-methyl -6-[(1-iminoethyl)amino]-4-hexenoic acid;

(S,E)-2-amino-2-methyl-6-[(1-iminoethyl)amino]-4-hexenoic acid;

(2S,4E)-2-amino-2-methyl-6-(3-methyl-5-oxo-1,2,4-oxadiazol-4(5H)-yl)hex-4-enoic acid;

(2S,4E)-2-amnio-6{[(1Z-N-hydroxyl)ethanimidoyl]amino}-2-methylhex-4-enoic acid;

(E)-2-amino-2-methyl-6-[(1-iminoethyl)amino]-4-hexenoic acid, dihydrochloride;

(S,E)-2-amino-2-methyl-5-fluoro-6-[(1-iminoethyl)amino]-4-hexenoic acid, dihydrochloride;

(S,E)-2-amino-2-methyl-4-fluoro-6-[(1-iminoethyl)amino]-4-hexenoic acid, dihydrochloride;

(S,E)-2-amino-2-methyl-4,5-difluoro-6-[(1-iminoethyl)amino]-4-hexenoic acid, dihydrochloride;

(R,E)-2-amino-2-methyl-6-[(1-iminoethyl)amino]-4-hexenoic acid, dihydrochloride;

(S,E)-2-amino-2-methyl-6-[(1-iminoethyl)amino]-4-hexenoic acid, dihydrochloride;

2-amino-2-methyl-6-[(1-iminoethyl)amino]-4-hexynoic acid, dihydrochloride;

(Z)-2-amino-2-methyl-6-[(1-iminoethyl)amino]-4-hexenoic acid, dihydrochloride;

(S,E)-2-amino-2-methyl-6-[(1-iminoethyl)amino]-4-hexenoic acid, dihydrochloride; and (2S,4E)-2-amino-2-methyl-6-(3-methyl-5-oxo-1,2,4-oxadiazol-4(5H)-yl)hex-4-enoic acid hydrochloride.

204. A pharmaceutical composition comprising at least one compound selected from the group consisting of:

(E)-2-amino-2-methyl-6-[(1-iminoethyl)amino]-4-hexenoic acid;

(S,E)-2-amino-2-methyl-5-fluoro-6-[(1-iminoethyl)amino]-4-hexenoic acid;

(S,E)-2-amino-2-methyl-4-fluoro-6-[(1-iminoethyl)amino]-4-hexenoic acid;

(S,E)-2-amino-2-methyl-4,5-difluoro-6-[(1-iminoethyl)amino]-4-hexenoic acid;

(R,E)-2-amino-2-methyl -6-[(1-iminoethyl)amino]-4-hexenoic acid;

(S,E)-2-amino-2-methyl-6-[(1-iminoethyl)amino]-4-hexenoic acid;

2-amino-2-methyl-6-[(1-iminoethyl)amino]-4-hexynoic acid;

(Z)-2-amino-2-methyl-6-[(1-iminoethyl)amino]-4-hexenoic acid;

(S,E)-2-amino-2-methyl-6-[(1-iminoethyl)amino]-4-hexenoic acid;

(2S,4E)-2-amino-2-methyl-6-(3-methyl-5-oxo-1,2,4-oxadiazol-4(5H)-yl)hex-4-enoic acid;

(2S,5E)-2-amnio-6{[(1Z-N-hydroxyl)ethanimidoyl]amino}-2-methylhex-4-enoic acid;

(E)-2-amino-2-methyl-6-[(1-iminoethyl)amino]-4-hexenoic acid, dihydrochloride;

(S,E)-2-amino-2-methyl-5-fluoro-6-[(1-iminoethyl)amino]-4-hexenoic acid, dihydrochloride;

(S,E)-2-amino-2-methyl-4-fluoro-6-[(1-iminoethyl)amino]-4-hexenoic acid, dihydrochloride;

(S,E)-2-amino-2-methyl-4,5-difluoro-6-[(1-iminoethyl)amino]-4-hexenoic acid, dihydrochloride;

(R,E)-2-amino-2-methyl-6-[(1-iminoethyl)amino]-4-hexenoic acid, dihydrochloride;

(S,E)-2-amino-2-methyl-6-[(1-iminoethyl)amino]-4-hexenoic acid, dihydrochloride;

2-amino-2-methyl-6-[(1-iminoethyl)amino]-4-hexynoic acid, dihydrochloride;

(Z)-2-amino-2-methyl-6-[(1-iminoethyl)amino]-4-hexenoic acid, dihydrochloride;

(S,E)-2-amino-2-methyl-6-[(1-iminoethyl)amino]-4-hexenoic acid, dihydrochloride; and (2S,4E)-2-amino-2-methyl-6-(3-methyl-5-oxo-1,2,4-oxadiazol-4(5H)-yl)hex-4-enoic acid hydrochloride.

* * * * *